United States Patent [19]

Schwartz et al.

[11] Patent Number: 5,728,581
[45] Date of Patent: Mar. 17, 1998

[54] METHOD OF EXPANDING HEMATOPOIETIC STEM CELLS, REAGENTS AND BIOREACTORS FOR USE THEREIN

[75] Inventors: Richard Merrill Schwartz, San Mateo; Sean Newton Tucker, San Francisco; Srikanth Ranga Chary, Fremont; Suzanne Chang Kuo, Cupertino, all of Calif.

[73] Assignee: Systemix, Inc., Palo Alto, Calif.

[21] Appl. No.: 482,259

[22] Filed: Jun. 7, 1995

[51] Int. Cl.⁶ .............. C12N 5/00; C12N 5/02; C12M 1/22
[52] U.S. Cl. ............. 435/385; 435/297.1; 435/325; 435/372; 435/383; 435/384; 435/385
[58] Field of Search ............ 435/240.2, 240.21, 435/240.25, 240.1, 297.2, 325, 372, 383, 384, 385

[56] References Cited

U.S. PATENT DOCUMENTS

| | | | |
|---|---|---|---|
| 4,201,845 | 5/1980 | Feder et al. | 435/297.2 |
| 4,225,671 | 9/1980 | Puchinger et al. | 435/70.3 |
| 4,296,205 | 10/1981 | Verma | 435/401 |
| 4,495,288 | 1/1985 | Jarvis, Jr. et al. | 435/382 |
| 4,661,455 | 4/1987 | Hubbard | 435/401 |
| 4,714,680 | 12/1987 | Civin | 435/347 |
| 4,722,902 | 2/1988 | Harm et al. | 435/297.4 |
| 4,789,634 | 12/1988 | Müller-Lierheim et al. | 435/181 |
| 4,804,628 | 2/1989 | Cracauer et al. | 435/400 |
| 4,839,292 | 6/1989 | Cremonese | 435/297.2 |
| 4,889,812 | 12/1989 | Guinn et al. | 435/286.7 |
| 4,937,196 | 6/1990 | Wrasidlo et al. | 435/297.2 |
| 4,963,489 | 10/1990 | Naughton et al. | 435/1.1 |
| 4,999,298 | 3/1991 | Wolfe et al. | 435/400 |
| 5,015,585 | 5/1991 | Robinson | 435/401 |
| 5,017,490 | 5/1991 | Taiariol et al. | 435/401 |
| 5,032,507 | 7/1991 | Yu et al. | 424/93.73 |
| 5,061,620 | 10/1991 | Tsukamoto et al. | 435/7.21 |
| 5,068,195 | 11/1991 | Howell et al. | 435/297.2 |
| 5,126,238 | 6/1992 | Gebhard et al. | 435/3 |
| 5,135,853 | 8/1992 | Dziewulski et al. | 435/41 |
| 5,139,946 | 8/1992 | Howell et al. | 435/401 |
| 5,149,649 | 9/1992 | Miyamori et al. | 435/400 |
| 5,158,881 | 10/1992 | Aebischer et al. | 435/182 |
| 5,160,490 | 11/1992 | Naughton et al. | 435/287.1 |
| 5,166,065 | 11/1992 | Williams et al. | 435/377 |
| 5,409,825 | 4/1995 | Hoffman et al. | 435/240.1 |

FOREIGN PATENT DOCUMENTS

| | | |
|---|---|---|
| 0112155 | 6/1984 | European Pat. Off. |
| 0155237 | 9/1985 | European Pat. Off. |
| 0220650 | 5/1987 | European Pat. Off. |
| 0356785 | 3/1990 | European Pat. Off. |
| 0412621 | 2/1991 | European Pat. Off. |
| 0419234 | 3/1991 | European Pat. Off. |
| 0420171 | 4/1991 | European Pat. Off. |
| 0475303 | 3/1992 | European Pat. Off. |
| 0480400 | 4/1992 | European Pat. Off. |
| 0550769 | 7/1993 | European Pat. Off. |
| 0112154 | 6/1984 | WIPO |
| WO 86/02379 | 4/1986 | WIPO |
| WO 87/06120 | 10/1987 | WIPO |
| WO 89/00188 | 1/1989 | WIPO |
| WO 89/11529 | 11/1989 | WIPO |
| WO 90/13639 | 11/1990 | WIPO |
| WO 90/15859 | 12/1990 | WIPO |
| WO 90/15877 | 12/1990 | WIPO |
| WO 91/18972 | 12/1991 | WIPO |
| WO 92/11355 | 7/1992 | WIPO |
| WO 92/13940 | 8/1992 | WIPO |
| WO 92/18615 | 10/1992 | WIPO |
| WO 93/08268 | 4/1993 | WIPO |
| WO 93/18137 | 9/1993 | WIPO |
| WO 94/05775 | 3/1994 | WIPO |
| WO 94/18991 | 9/1994 | WIPO |
| WO 95/03693 | 2/1995 | WIPO |
| WO 95/05843 | 3/1995 | WIPO |
| WO 95/08105 | 3/1995 | WIPO |

OTHER PUBLICATIONS

Koller et al. (1992a) Exp. Hematol. vol. 20:264–270.
Koller et al (1992b) Ann. N.Y. Acad. Sci. vol. 665:105–116.
Smith et al (1986) Br. J. Haematol. vol. 63(1) 29–34–Abstract Attached.
Schwartz et al. (1994) Abstract–#2289, Blood, vol. 84 (10, Suppl. 1).
Koller et al. (1992) Blood, vol. 80(2):403–411.
Palsson et al (1993) Bio/Technology vol. 11(3):368–372–Abstract Attached.
Schwartz et al. (1991) PNAS, USA, vol. 88:6760–6764.
"The Influence of Oxygen Tension on the Long–term Growth in vitro of Haematopoietic Progenitor Cells from Human Cord Blood", *British Journal of Haematology* (1986) 63:29–34.
Dexter et al., "Conditions controlling the proliferation of haemopoietic stem cells in vitro" *J. Cell. Physiol.* (1976) 91:335–344.

(List continued on next page.)

*Primary Examiner*—Leon B. Lankford, Jr.
*Assistant Examiner*—Christopher R. Tate
*Attorney, Agent, or Firm*—Morrison & Foerster LLP

[57] ABSTRACT

The present invention provides methods and bioreactors for expanding stem cells in a population of cells substantially enriched in hematopoietic stem cells and substantially free of stromal cells. The method comprising the steps of inoculating the population of cells in an expansion container in a volume of suitable medium such that the cell density is at least about 5,000 cells/1 mL and at an initial oxygen concentration of less than 8%; adding an effective amount of at least one cytokine to cause stem cell expansion; culturing the cells under suitable conditions such that the cells condition the medium; increasing the oxygen concentration to about 20%; exchanging the medium at a rate which allows expansion of the stem cells; and culturing the cells under conditions such that the stem cells are expanded. The present invention also provides a bioreactor constructed to accommodate the operational requirements for stroma-free stem cell expansion.

19 Claims, 13 Drawing Sheets

OTHER PUBLICATIONS

Kyoizumi et al., "Implantation and maintenance of functional human bone marrow in SCID–hu mice" *Blood* (1992) 79:1704–1711.

Murray et al., "Enrichment of human hematopoietic stem cell activity in the CD34+Thy–1 +Lin–subpopulation from mobilized peripheral blood" *Blood* (1995) 85:368–378.

Zanjani et al., "Engraftment and long–term expression of human fetal hemopoietic stem cells in sheep following transplantation in utero" *J. Clin. Invest.* (1992) 89:1178–1188.

Srour et al., "Animal models for human hematopoiesis" *J. Hematotherapy* (1992) 1:143–153.

Sutherland et al., "Functional characterization of individual human hematopoietic stem cells cultured at limiting dilution on supportive marrow stromal layers" *Proc. Natl. Acad. Sci USA* (1990) 87:3584–3588.

Breems et al., "Frequency analysis of human primitive haematopoietic stem cell subsets using a cobblestone area forming cell assay" *Leukemia* (1994) 8:1095–1104.

Craig et al., "Expression of Thy–1 on human hematopoietic progenitor cells" *J. Exp. Med.* (1993) 177:1331–1342.

Sutherland et al. "Differential sensitivity of CD34 epitopes to cleavage by *Pasteurella haemolytica* glycoprotease: Implications for purification of CD34–positive progenitor cells" *Exp. Hematol.* (1992) 20:590–599.

Marsh et al., "Retention of progenitor cell function in CD34+cells purified using a novel O–sialoglycoprotease" *Leukemia* (1992) 6:926–934.

Srour et al., "Long–term generation and expansion of human primitive hematopoietic progenitor cells in vitro" *Blood* (1993) 81:661–669.

Palsson et al., "Expansion of human bone marrow progenitor cells in a high cell density continuous perfusion system" *BioTechnol.* (1993) 11:368–372.

Katahira et al., "Improvement of culture conditions for human megakaryocytic and pluripotent progenitor cells by low oxygen tension" *Int. J. Cell Cloning* (1987) 5:412–420.

Watanabe et al., "Development of T cell receptor αβ–bearing T cells in the submersion organ culture of murine fetal thymus at high oxygen concentration" *Eur. J. Immunol.* (1993) 23:200–205.

Broxmeyer et al., "A rapid proliferation assay for unknown co–stimulating factors in cord blood plasma possibly involved in enhancement of in vitro expansion and replating capacity of human hematopoietic stem/progenitor cells" *Blood Cells* (1994) 20:492–497.

Clarke, "Retroviral gene transfer into human hematopoietic cells using rapidly perfused long–term bone marrow cultures" *Cancer Bull.* (1993) 45:153–158.

Edgington, "New horizons for stem–cell bioreactors" *Bio/Technol.* (1992) 10:1099–1107.

Edgington, "A new force in biotech: Tissue engineering" *Bio/Technol.* (1994) 12:361–364.

Emerson et al., "The construction of high efficiency human bone marrow tissue ex vivo" *J. Cell. Biochem.* (1991) 45:268–272.

Ishikawa et al., "Kinetics of hemopoietic stem cells in a hypoxic culture" *Eur. J. Haemotol.* (1988) 40:126–129.

Koller, "Expansion of human hematopoietic progenitors with synergistic cytokine combinations in a perfusion bioreactor" *J. Cell Biochem.* (1992) 16 (Part F): p. 135 (abstract CE 302).

Koller et al., "Reduced oxygen tension increases hematopoiesis in long–term culture of human stem and progenitor cells from cord blood and bone marrow" *Exp. Hematol.* (1992) 20:264–270.

Koller et al., "Effects of synergistic cytokine combinations, low oxygen, and irradiated stroma on the expansion of human cord blood progenitors" *Blood* (1992) 80:403–411.

Koller et al., "Beneficial effects of reduced oxygen tension and perfusion in long–term hematopoietic cultures" *Biochem. Eng. VII* (1992) 915:1–15.

Koller et al., "Tissue engineering: Reconstitution of human hematopoiesis ex vivo" *Biotechnology and Bioengineering* (1993) 42:909–930.

Koller et al., "Large–scale expansion of human stem and progenitor cells from bone marrow mononuclear cells in continuous perfusion cultures" *Blood* (1993) 82:378–384.

Koller et al., "Expansion of CD34–enriched human bone marrow cells: Effects of feeding schedule, cytokines, and stroma" *Exper. Hematol.* (1994) 22: p. 726 (abstract no. 181).

Lemoli et al., "Proliferation of human hematopoietic progenitors in long–term bone marrow cultures in gas–permeable plastic bags is enhanced by colony–stimulating factors" *Exp. Hematol.* (1992) 20:569–575.

Oh et al., "Frequent harvesting from perfused bone marrow cultures results in increased overall cell and progenitor expansion" *Biotechnology and Bioengineering* (1994) 44:609–616.

Palsson, "Reconstruction of human bone marrow ex vivo: Culture optimization and potential applications" *Ann. Biomed. Eng.* (1991) 19:599–600 (abstract 91–143).

Palsson, "The productivity and longevity of human bone marrow cultures is significantly enhanced by the medium perfusion rate and added hematopoietic growth factors" *Cell. Biochem.* (1991) Supplement 15F, p. 147.

Sardonini et al., "Expansion and differentiation of human hematopoietic cells from static cultures through small–scale bioreactors" *Biotechnol. Prog.* (1993) 9:131–137.

Schwartz et al., "Stimulation fo hematopoiesis in vitro by the combination of physiologic medium perfusion schedules and supplementation of hematopoietic growth factors" *Blood* (1994) 84:118a (abstract 463).

Schwartz et al., "Rapid medium perfusion rate significantly increases the productivity and longevity of human bone marrow cultures" *Proc. Natl. Acad. Sci. USA* (1991) 88:6760–6764.

Schwartz et al., "In vitro myelopoiesis stimulated by rapid medium exchange and supplementation with hematopoietic growth factors" *Blood* (1991) 78:3155–3161.

Van Zant et al., "Expansion in bioreactors of human progenitor populations from cord blood and mobilized peripheral blood" *Blood Cells* (1994) 20:482–491.

Wang et al., "Multilineal hematopoiesis in a three–dimensional murine long–term bone marrow culture" *Exper. Hematol.* (1995) 23:26–32.

Young et al., "Retention of quiescent hematopoietic cells with high proliferative potential during ex vivo stem cell culture" *Blood* (1994) 84:126a (abstract 490).

Koller et al., "Beneficial effects of reduced oxygen tension and perfusion in long–term hematopoietic cultures" *Ann. New York Acad. Sci.* (1992) 665:105–116.

Schwartz et al., "Ex vivo production of progenitor cells from purified CD34++THY–1+Lin–hematopoietic stem cells" *Blood* (1994) 84(10) (Suppl. 1):576A. (abstract no. 2289).

- ● TISSUE 2 – CELLS MOVED TO 21% DAY 12
- ■ TISSUE 2 – OXYGEN CAMILE CONTROLLED
- ◇ TISSUE 1 – CONSTANT 5%
- □ TISSUE 1 – CAMILE CONTROLLED
- ▽ TISSUE 3 – CONSTANT 5%
- △ TISSUE 3 – CONSTANT 21%
- + TISSUE 3 – INCREASE ON DAY 14
- * TISSUE 3 – INCREASE ON DAY 18
- ○ TISSUE 3 – CAMILE CONTROLLED
- ▲ TISSUE 2 – CELLS MOVED TO 21% DAY 9
- ◆ TISSUE 2 – CONSTANT 5% O2

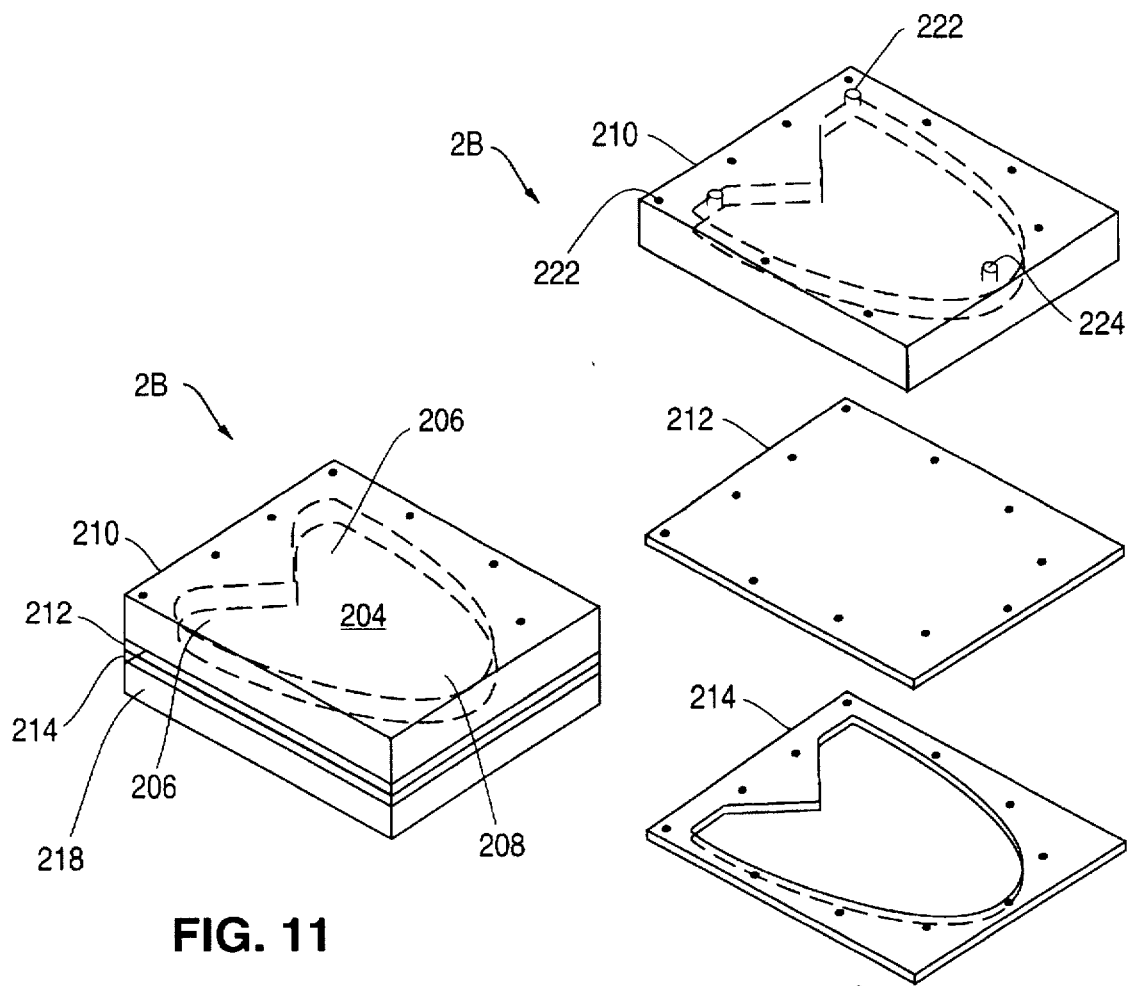
FIG. 11
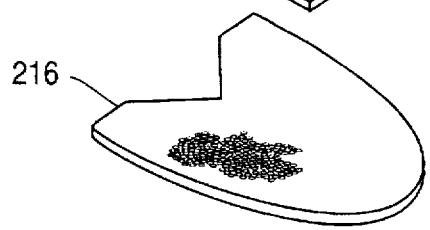
FIG. 12
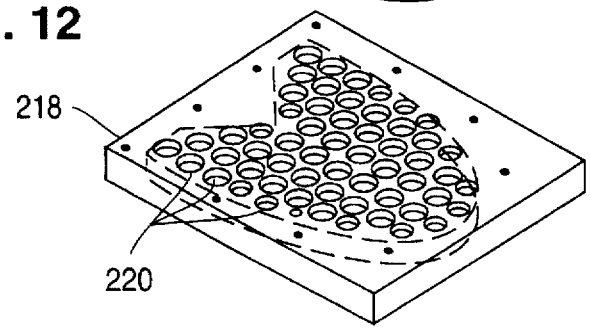

5,728,581

METHOD OF EXPANDING HEMATOPOIETIC STEM CELLS, REAGENTS AND BIOREACTORS FOR USE THEREIN

FIELD OF THE INVENTION

The present invention relates to expansion of human hematopoietic stem cells. Methods for expansion are provided as are bioreactors suitable for use therein.

BACKGROUND OF THE INVENTION

Blood cell production derives from a single type of cell, the hematopoietic stem cell which through proliferation and differentiation, gives rise to the entire hematopoietic system. The hematopoietic stem cells are believed to be capable of self-renewal—expanding their own population of stem cells—and they are pluripotent—capable of differentiating into any cell in the hematopoietic system. From this rare cell population, the entire mature hematopoietic system, comprising lymphocytes (B and T cells of the immune system) and myeloid cells (erythrocytes, megakaryocytes, granulocytes and macrophages) is formed. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides red blood cells, which act as oxygen carriers. As used herein, "stem cell" refers to hematopoietic stem cells and not stem cells of other cell types.

Transplantation of bone marrow, either autologous or allogeneic, can replace a functional hematopoietic system after myelosuppressive or myeloablative chemotherapy as a treatment for cancer. In addition, purified stem cells may be reinfused into the patient to restore hematopoiesis in these compromised patients. It also has been found that administration of chemotherapeutic agents and/or cytokines mobilizes bone marrow stem cells into the peripheral blood such that peripheral blood can be harvested as a source of stem cells. In an autologous transplant setting it is often particularly desirable to purify stem cells from the bone marrow or peripheral blood to use as a graft as a way of purifying long-term repopulating cells free of contaminating tumor cells. Tumor has been detected as high as 10% in mobilized peripheral blood collections and up to 80% in the mononuclear fraction from marrow.

Unlike whole bone marrow, stem cell replacement does not restore mature hematopoietic cells immediately. Due to the time necessary to generate mature cells from reinfused stem cells, there is a lag during which the patient remains immunocompromised. One proposed solution has been to expand the purified (and tumor-free) stem cells ex vivo to generate a cell population having both stem cells and slightly more differentiated cells, which would be able to provide both short- and long-term hematopoietic recovery.

Methods of bone marrow expansion have been developed, however, expansion of stem cells is not as straight-forward as expansion from a mature population. First, stem cells are very rare and, therefore, the number of stem cells isolated from any source will be very small. This reduces the size of the population that can be used to initiate the culture system. Second, the goal in stem cell expansion is not just to produce large quantities of mature cells, but also to retain stem cells and to produce many immature progenitor cells, which are capable of rapidly proliferating and replenishing mature cell types depleted in the patient. Upon reinfusion into a patient, the mature cells are cleared quickly whereas stem cells home to the marrow where long-term engraftment can occur. In addition, the immature progenitor cells can produce more cell types and more numbers of cells than the mature cells, thus providing short-term hematopoietic recovery.

One method of stem cell culture in vitro utilizes an adherent monolayer of stromal cells, which supports the viability of stem and early progenitor cells ("Dexter culture"; see Dexter et al. (1976) *J. Cell Phys.* 9:335). For clinical use, however, it is preferable to utilize a more easily defined stromal-free culture system. U.S. Pat. No. 5,409,825 describes stroma-free stem cell expansion. In addition, a closed bioreactor expansion system is necessary to obtain a clinical acceptable expanded stem cell population.

Accordingly, a need exists for methods and systems for efficient culture and expansion of stem cells under controlled conditions that will yield suitable numbers of stem/progenitor cells for clinical use. This invention satisfies these needs and provides related advantages as well.

SUMMARY OF THE INVENTION

The present invention provides methods and bioreactors for expanding a population of cells substantially enriched in hematopoietic stem cells and substantially free of stromal cells. The method comprises the steps of inoculating the population of cells in an expansion container in a volume of a suitable medium such that the initial cell density is at least 5,000 cells/1 mL and at an initial oxygen concentration of 2 to 8%; adding an effective amount of at least one cytokine to cause stem cell expansion; culturing the cells under suitable conditions such that the cells condition the medium; increasing the oxygen concentration to about 20%; exchanging the medium at a rate which allows expansion of the stem cells; and culturing the cells under conditions such that the stem cells are expanded.

The present invention also provides a bioreactor constructed to accommodate the operational requirements for stroma-free stem cell expansion.

In a preferred embodiment, the bioreactor comprises a rigid housing that defines a chamber having an upstream end portion and a downstream end portion. The bioreactor further includes multiple ports formed through the housing. These ports are in the vicinity of the upstream and downstream end portions and are in fluid communication with the chamber. The number of ports in the vicinity of one of the upstream and downstream portions is greater than the number of ports in the vicinity of the other one of those portions to minimize flow channeling, for example. The ports are adapted for selective coupling to one medium source and a collection or waste receptacle so that medium can be introduced into the chamber in the vicinity of the upstream portion, flow over cells placed in the chamber and be discharged from the outlet port where they can be collected in a waste receptacle. With this construction, a compact bioreactor that facilitates uniform flow over cells placed therein is provided. More specifically, the multiple inlet port per outlet port (or vice versa) configuration minimized or eliminates a possibility of the medium flow through the chamber from channeling. Otherwise, there would be dead spaces in the bioreactor where cells may not receive any or sufficient medium for proper cell growth.

In a preferred embodiment, the bioreactor has two inlet ports for providing medium in the upstream portion of the bioreactor chamber and one outlet port arranged for discharging medium from the downstream portion of the chamber. This configuration allows a more compact design than a single input to single output which would be substantially longer for the same chamber capacity and, thus, more difficult to handle in a laboratory environment, while maintaining the number of inlet and outlet ports to a minimum, thereby avoiding complex pump and tube arrangements.

The rigid feature of the bioreactor also facilitates providing a constant chamber configuration that will provide optimal fluid flow therethrough for any given number of inlet and outlet ports. Thus, in a two-inlet port to one-outlet port arrangement, the working area of the chamber which confines the cells and medium can be maintained in a constant optimal shape to optimize fluid flow and provide even flow over the cells for optimal cell growth. More specifically, with the two-inlet to one-outlet configuration, a preferred chamber configuration includes a first portion to which the medium is introduced and a second portion to which the introduced medium flows through to reach the outlet port. The second portion has a shape generally corresponding to one half of an ellipse.

According to another aspect of the invention, the bioreactor can be provided with a reduced volume space to start the culture which is especially advantageous when expanding stroma-free cell cultures. When dealing with stroma-free stem cells, there is a minimum inoculation density to produce the requisite number of cells such as $CD34^+$ cells. Applicants have found that this number is at least about 5,000, preferably at least about 7,000 and most preferably about 20,000 (BM 7–20,000 cells/mL; MPB 20–50,000 cells/mL) stem cells/mL. In the preferred embodiment, the bioreactor is provided with a depression or recess in the bottom surface of the housing that faces and defines the chamber in the upstream portion of the chamber. This depression allows for the initial placement of the cells in a reduced space of the chamber or small area of the chamber so that they can pack closer together to start and thereby form a local increase in cell concentration.

According to another aspect of the invention, a headspace is preferably incorporated into the bioreactor. This is generally accomplished by providing the chamber in the bioreactor with a volume that is substantially greater than the cells and cell medium therein. According to this embodiment, the wall of the bioreactor that forms or defines the bottom of the chamber is gas impermeable and a vent is provided in the bioreactor housing to provide the free exchange of air between the chamber and the outside of the bioreactor. With this construction, the gas headspace above the surface of the cells and cell medium provides continuous gas transfer to and from the cells.

The above is a brief description of some of the aspects, features and advantages of the present invention. Other aspects, features, advantages and embodiments of the invention will be apparent to those skilled in the art from which the following description, accompanying drawings and appended claims.

BRIEF DESCRIPTION OF THE DRAWINGS

FIG. 11 is a perspective view of a further bioreactor constructing according to the principles of the present inventions.

FIG. 12 is an exploded view of the bioreactor of FIG. 11.

FIG. 16A schematically illustrates the initial cell population, while FIG. 16B illustrates the same cell population expanded according to the present invention.

DETAILED DESCRIPTION OF THE INVENTION

Figure 1:
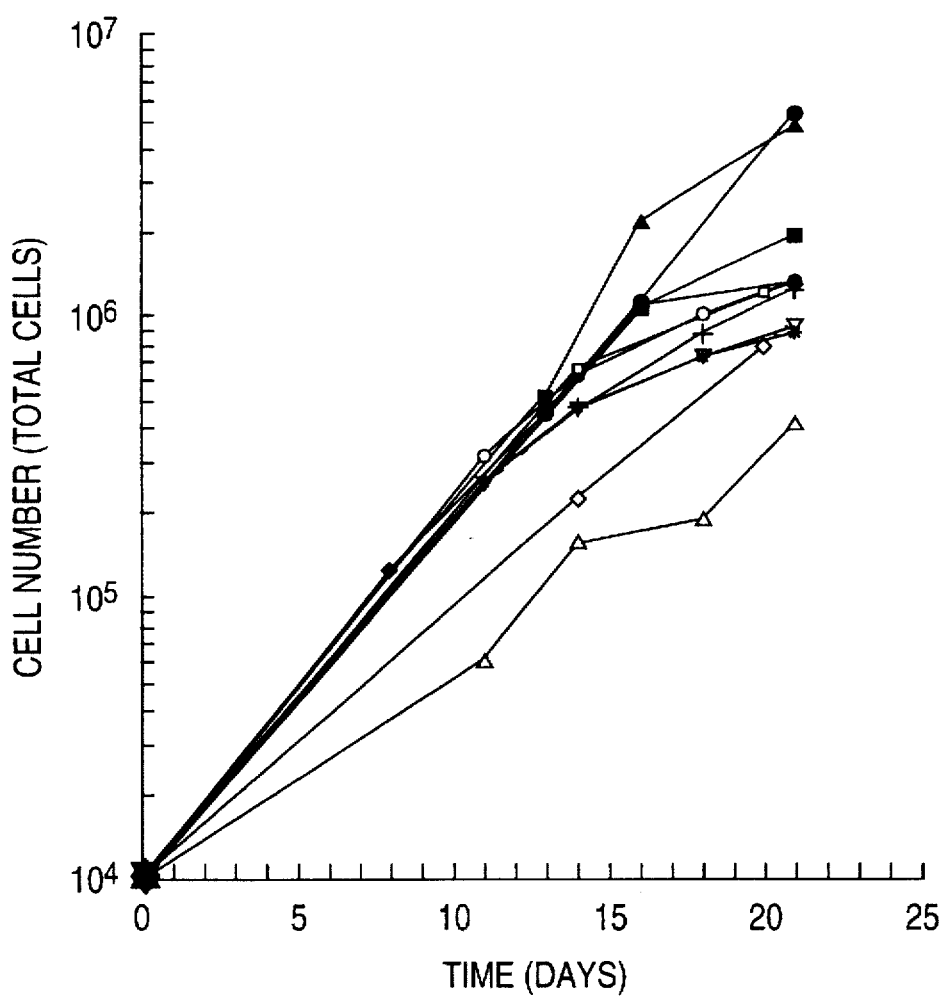
FIG. 1 graphically shows the relationship between oxygen ramping and total cell number. For each case, increasing the oxygen during expansion increased the total cells that were produced.

This invention provides a method of expanding a population of cells substantially enriched in hematopoietic stem cells and substantially free of stromal cells. The method is useful for expansion of stem cells in closed, perfusable, culture containers. A "closed culture" is one which allows for the necessary cell distribution, introduction of nutrients and oxygen, removal of waste metabolic products, optional recycling of hematopoietic cells and harvesting of hematopoietic cells without exposing the culture to the external environment, and does not require manual feeding or manual manipulation before the cells are harvested.

This invention also provides a bioreactor for accomplishing this method. In one aspect of this invention, the culture has an expandable culture volume.

As used herein, "stem cells" refers to animal, especially mammalian, preferably human, hematopoietic stem cells and not stem cells of other cell types. "Stem cells" also refers to a population of hematopoietic cells having all of the long-term engrafting potential in vivo. Animal models for long-term engrafting potential of candidate human hematopoietic stem cell populations include the SCID-hu bone model (Kyoizumi et al. (1992) *Blood* 79:1 704; Murray et al. (1995) *Blood* 85(2) 368–378) and the in utero sheep model (Zanjani et al. (1992) *J. Clin. Invest.* 89:1179). For a review of animal models of human hematopoiesis, see Srour et al. (1992) *J. Hematother.* 1:143–153 and the references cited therein. At present, the best in vitro assay for stem cells is the long-term culture-initiating cell (LTCIC) assay, based on a limiting dilution analysis of the number of clonogenic cells produced in a stromal co-culture after 5–8 weeks. Sutherland et al. (1990) *Proc. Nat'l Acad. Sci.* 87:3584–3588. The LTCIC assay has been shown to correlate with another commonly used stem cell assay, the cobblestone area forming cell (CAFC) assay, and with long-term engrafting potential in vivo. Breems et al. (1994) *Leukemia* 8:1095.

For use in the present invention, a highly enriched stem cell population is preferred in order to maximize the content of stem and early progenitor cells in the expanded cell population. An example of an enriched stem cell population is a population of cells selected by expression of the CD34 marker. In LTCIC assays, a population enriched in CD34$^+$ cells will have an LTCIC frequency in the range of 1/50 to 1/50, more usually in the range of 1/50 to 1/200. Preferably, the stem cell population will be more highly enriched for stem cells than that provided by a population selected on the basis of CD34$^+$ expression alone. By use of various techniques described more fully below, a highly enriched stem cell population may be obtained. A highly enriched stem cell population will typically have an LTCIC frequency in the range of 1/5 to 1/100, more usually in the range of 1/10 to 1/50. Preferably it will have an LTCIC frequency of at least 1/50. Exemplary of a highly enriched stem cell population is a population having the CD34$^+$\Thy-1$^+$\LIN$^-$ phenotype as described in U.S. Pat. No. 5,061,620. A population of this phenotype will typically have an average LTCIC frequency of approximately 1/20. Murray et al. (1995) supra; Lansdorp et al. (1993) *J. Exp. Med.* 177:1331. It will be appreciated by those of skill in the art that the enrichment provided in any stem cell population will be dependent both on the selection criteria used as well as the purity achieved by the given selection techniques.

As used herein, the term "expansion" is intended to mean an increase in cell number from the pluripotent stem cells used to initiate the culture. "Substantially free of stromal cells" shall mean a cell population which, when placed in a culture system as described herein, does not form an adherent cell layer.

The hematopoietic stem cells used to inoculate the cell culture may be derived from any source including bone marrow, both adult and fetal, cytokine or chemotherapy mobilized peripheral blood, fetal liver, bone marrow or umbilical cord blood.

In general, it is desirable to isolate the initial inoculation population from neoplastic cells prior to culture. Separation of stem cells from neoplastic cells can be performed by any number of methods, including cell sorters, magnetic beads, packed columns. Isolation of the phenotype (CD34$^+$Thy-1$^+$CD14$^-$CD15$^-$) from multiple myeloma patients has been shown to reduce the tumor burden to less than 1 tumor per 10$^5$ purified cells.

In other aspects, it is desirable to enrich the inoculation population for CD34$^+$ cells prior to culture, using for example, the method of Sutherland et al. (1992) *Exp. Hematol.* 20:590 and that described in U.S. Pat. No. 4,714,680. Preferably, the cells are subject to negative selection to remove those cells that express lineage specific markers. Methods of negative selection are known in the art. As used herein, lineage-negative (LIN$^-$) refers to cells lacking at least one marker associated with lineage committed cells, e.g., markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils or other markers such as CD38, CD71, and HLA-DR. Preferably the lineage specific markers include, but are not limited to, at least one of CD2, CD14, CD15, CD16, CD19, CD20, CD33, CD38, HLA-DR and CD71. More preferably, LIN$^-$ will include at least CD14 and CD15. Further purification can be achieved by positive selection for, e.g., c-kit$^+$ or Thy-1$^+$. Further enrichment can be obtained by use of the mitochondrial binding dye rhodamine 123 and selection for rhodamine$^{lo}$ cells, by methods known in the art. A highly enriched composition can be obtained by selective isolation of cells that are CD34$^+$, preferably CD34+LIN$^-$, and most preferably, CD34$^+$Thy-1$^+$LIN$^-$. Populations highly enriched in stem cells and methods for obtaining them are described in PCT/US94/09760; PCT/US94/08574 and PCT/US94/10501.

The expansion method requires inoculating the population of cells substantially enriched in hematopoietic stem cells and substantially free of stromal cells into an expansion container and in a volume of a suitable medium such that the cell density is from at least about 5,000, preferably 7,000 to about 200,000 cells/mL of medium, and more preferably from about 10,000 to about 150,000 cells/mL of medium, and at an initial oxygen concentration of from about 2 to 20% and preferably less than 8%. In one embodiment, the initial oxygen concentration is in a range from about 4% to about 6%. In one aspect, the inoculating population of cells is derived from bone marrow and is from about 7,000 cells/mL to about 20,000 cells/mL and preferably about 20,000 cell/mL. In a separate aspect, the inoculation population of cells is derived from mobilized peripheral blood and is from about 20,000 cells/mL to about 50,000 cells/mL, preferably 50,000 cells/mL.

Any suitable expansion container, flask, or appropriate tube such as a 24 well plate, 12.5 cm$^2$ T flask or gas-permeable bag can be used in the method of this invention. Such culture containers are commercially available from Falcon, Corning or Costor. As used herein, "expansion container" also is intended to include any chamber or containor for expanding cells whether or not free standing or incorporated into an expansion apparatus such as the bioreactors described herein. In one embodiment, the expansion container is a reduced volume space of the chamber which is formed by a depressed surface and a plane in which a remaining cell support surface is orientated.

Various media can be used for the expansion of the stem cells. Illustrative media include Dulbecco's MEM, IMDM and RPMI-1640 that can be supplemented with a variety of different nutrients, growth factors, cytokines, etc. The media can be serum free or supplemented with suitable amounts of serum such as fetal calf serum or autologous serum. Preferably, if the expanded cells or cellular products are to be used in human therapy, the medium is serum-free or supplemented with autologous serum. One suitable medium is one containing IMDM, effective amounts of at least one of a peptone, a protease inhibitor and a pituitary extract and effective amounts of at least one of human serum albumin or plasma protein fraction, heparin, a reducing agent, insulin, transferrin and ethanolamine. In a further embodiment, the suitable expansion medium contains at least IMDM and 1–15% fetal bovine serum. Other suitable media formulations are those provided below, e.g. those designated SSP15 and SSP14. However, the most prefered media formulation for use in this invention is the media designated SSP16, as defined below.

TABLE 1

| components | IMDM | SSP | basal medium |
|---|---|---|---|
| arginine HCl | 0.084 | 0.1008 | 0.0504–0.1512 |
| choline chloride | 0.004 | 0.0048 | 0.0024–0.0072 |
| histidine HCl H$_2$O | 0.042 | 0.0504 | 0.0252–0.0756 |
| isoleucine | 0.105 | 0.126 | 0.063–0.189 |
| leucine | 0.105 | 0.126 | 0.063–0.189 |
| lysine HCl | 0.146 | 0.1752 | 0.0876–0.2628 |
| methionine | 0.03 | 0.036 | 0.0072–0.0432 |
| phenylalanine | 0.066 | 0.0792 | 0.0396–0.1188 |
| serine | 0.042 | 0.0504 | 0.0252–0.0756 |
| threonine | 0.095 | 0.114 | 0.057–0.171 |
| tryptophan | 0.016 | 0.0192 | 0.0096–0.0288 |
| tyrosine-2Na | 0.1038 | 0.12456 | 0.06228–0.18684 |
| valine | 0.094 | 0.1128 | 0.0564–0.1692 |
| biotin | 0.000013 | $1.56 \times 10^{-5}$ | $0.078$–$2.28 \times 10^{-5}$ |
| pantothenic acid | 0.004 | 0.0048 | 0.0024–0.0072 |
| niacinamide | 0.004 | 0.0048 | 0.0024–0.0072 |
| thiamine HCl | 0.004 | 0.0048 | 0.0024–0.0072 |
| riboflavin | 0.0004 | 0.00048 | 0.00024–0.00072 |
| folic acid | 0.004 | 0.0048 | 0.0024–0.0072 |
| potassium chloride | 0.33 | 0.396 | 0.198–0.594 |
| calcium chloride 2H$_2$O | 0.219 | 0.2628 | 0.1314–0.3942 |
| phenol red | — | — | — |
| pyruvic acid Na | 0.11 | 0.132 | 0.066–0.198 |
| asparagine H$_2$O | 0.0284 | 0.03408 | 0.01704–0.05112 |
| proline | 0.04 | 0.048 | 0.024–0.072 |
| vitamin B12 | 0.000013 | $1.56 \times 10^{-5}$ | $0.078$–$2.28 \times 10^{-5}$ |
| alanine | 0.025 | 0.03 | 0.015–0.045 |
| aspartic acid | 0.03 | 0.036 | 0.018–0.054 |
| glutamic acid | 0.075 | 0.09 | 0.045–0.135 |
| glycine | 0.03 | 0.036 | 0.018–0.054 |
| myoinositol | 0.0072 | 0.00864 | 0.00432–01296 |
| lipoic acid | 0.000105 | 0.000126 | 0.000063–0.000189 |
| sodium selinite | 0.000017 | $2.04 \times 10^{-5}$ | $1.02$–$3.06 \times 10^{-5}$ |
| cystine 2 HCl | 0.09124 | 0.109488 | 0.054744–0.164232 |
| 2-mercaptoethanol | 0.0036 | 0.00432 | 0.00216–0.00648 |
| HEPES | 5.958 | — | — |
| magnesium sulfate | 0.09767 | 0.117204 | 0.058602–0.175806 |
| potassium nitrate | 0.000076 | $9.12 \times 10^{-5}$ | $4.56$–$13.68 \times 10^{-5}$ |
| sodium phosphate monobasic | 0.109 | 0.1308 | 0.0654–0.1962 |
| pyroxidal | 0.004 | 0.0048 | 0.0024–0.0072 |
| glucose | 4.5 | 4.5 | 2.25–6.75 |
| sodium bicarbonate | 3.024 | 3.024 | 1.512–4.536 |
| glutamine | 0.584 | 0.7008 | 0.3504–1.0512 |
| dl-alphatocopherol | 0.00018 | 0.000216 | 0.000108–0.000324 |
| sodium chloride | 4.505 | — | — |
| sodium chloride use to adjust osmolality to 280 mOsm | | 4–5 G/L | — |

Several preferred combinations of media have been formulated. These are designated SSP12, SSP14, SSP15 and SSP16. These media have the following formulations, where SSP is the basal medium and has the formulation described in Table 1.

SSP12: 2% HSA, 20 IU/mL heparin, 2 mM 2-mercaptoethanol, $1\times10^{-5}$M each of insulin, transferrin and ethanolamine.

SSP14: in addition to components of SSP12, includes 2.5μg/L LDL, 0.2% meat peptone, $2\times10^{-5}$M linoleic acid, $2\times10^{-5}$M oleic acid, $2\times10^{-5}$M vitamin A, $2\times10^{-5}$M vitamin E, 10 KIU/mL aproptinin and 30 μl/mL pituitary extract.

SSP15: in addition to the components of SSP14, contains also 10 units/mL superoxide dismutase and $10^{-5}$M vitamin C.

SSP16: in addition to the components of SSP15, contains also $10^{-6}$M putrescine, vitamin B12, progesterone and testosterone at the preferred concentrations provided above.

As noted above, the medium formulations are supplemented with at least one cytokine at a concentration from about 0.1 ng/mL to about 500 ng/mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11 MIP-1α, LIF, c-mpl ligand/TPO, and flk2/flk3 ligand. Preferably, the culture will include at least c-kit ligand and IL-3. More preferably, the culture will include c-kit ligand, IL-3, IL-6 and GM-CSF. In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to 1/100 of the volume in the bioreactors with fresh cytokines being added approximately every 2 to 4 days. Further, fresh concentrated cytokines also can be added separately in addition, to cytokines in the perfused media.

The population is then cultured under suitable conditions such that the cells condition the medium. Applicants have found that improved expansion of purified stem cells is achieved when the culture medium is not changed, e.g., perfusion does not start until after the first several days of culture. Under such conditions, the stem cells appear to release one or more autocrine factors which aid in maintaining cell viability and expanding a more primitive cell population.

In most aspects, suitable conditions comprise culturing at 33 to 39, and preferably around 37° C. (the initial oxygen concentration is preferably 4–8%, and most preferably, about 5%) for at least 6 days and preferably from about 7 to about 10 days, to allow release of autocrine factors from the cells without release of sufficient waste products to substantially inhibit stem cell expansion. After that time, the oxygen concentration is preferably increased to about 20%, either stepwise or gradually over the remainder of the culture period, which will typically be for a total of 10–28 days. Preferably, bone marrow stem cells will be grown for around 21 days and mobilized peripheral blood stem cells will be cultured for around 14 days.

After the initial culture period without medium exchange, the culture medium is exchanged at a rate which allows expansion of the stem cells. In a system where no variable volume is used, medium is exchanged on day 7 (for MPB) or on day 10 (for BM). The exchange of fresh medium in a perfused system is preferably laminar. This uniform, nonturbulent, flow prevents the formation of "dead spaces" where patches of cells are not exposed to medium. The medium is exchanged at a rate of from about 0.10/day to 0.50 /day or 1/10 to 1/2 volume exchange per day. Preferably, the perfusion rate will be from about 0.25/day to 0.40/day. Most preferably, for bone marrow stem cells, perfusion will be at a rate of 0.27/day starting around day 14, and for mobilized peripheral blood stem cells, perfusion starts at 0.25 /day around day 10 and increases to 0.40/day around day 12.

Preferably, the cell concentration is kept at an optimum throughout expansion. For instance, stem cells can expand up to 1500 fold compared to a mononuclear cell (MNC) population which expands only 10–20 fold. Because stem cells have such a large proliferative capacity, a closed system must provide enough volume for total cell expansion. However, stem cells also require a relatively high inoculation density. The bioreactor described below solves this problem by providing "variable volume" operation. Thus, the cells are seeded at the appropriate cell density in a depression and additional media are added when an appropriate cell density is attained. The shape of the device allows the medium volume to be increased up to three-fold without significantly reducing the oxygen transfer efficiency to the cells.

This invention also provides a device for stroma-free expansion of stem cells in a closed perfusable chamber. In one embodiment, the bioreactor useful in this and other expansion methods comprises a rigid housing that defines a chamber having an upstream end portion and a downstream end portion. The bioreactor further includes multiple ports formed through the housing. These ports are in the vicinity of either the upstream and downstream end portions and are in fluid communication with the chamber. The number of ports in the vicinity of one of the upstream and downstream portions is greater than the number of ports in the vicinity of the other one of those portions. The ports are adapted for selective coupling to one of a medium source and a collection or waste receptacle so that medium can be introduced into the chamber in the vicinity of the upstream portion, flow over cells placed in the chamber and be discharged in the vicinity of the downstream portion where they can be collected in a waste receptacle. With this construction, a compact bioreactor that facilitates uniform flow over cells placed therein is provided. More specifically, the multiple inlet port per outlet port (or vice versa) configuration minimizes or reduces the possibility of channeling the medium flow through the chamber. Otherwise, there would be dead spaces in the reactor where cells may not receive any or sufficient fresh medium for proper cell growth.

In a further embodiment, the bioreactor has two inlet ports for providing medium in the upstream portion of the bioreactor chamber and one outlet port arranged for discharging medium from the downstream portion of the chamber. The configuration allows a more compact design than a single input to single output which would be substantially longer and, thus, more difficult to handle in a laboratory environment, while maintaining the number of inlet and outlet ports to a minimum, thereby avoiding complex pump and tube arrangements.

Figure 18A:
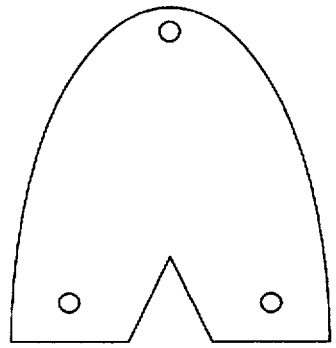
FIG. 18 shows optional bioreactor configurations.
Figure 18B:
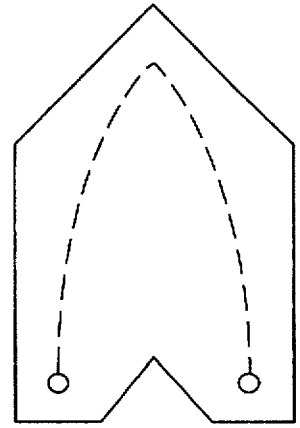
Figure 18C:
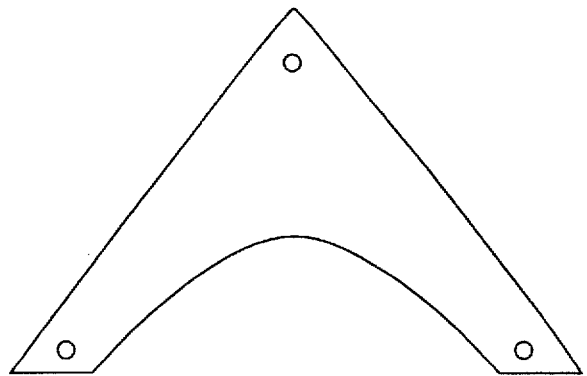

The rigid feature of the bioreactor also facilitates providing a constant chamber configuration that will provide optimal fluid flow therethrough for any given number of inlet and outlet ports. Thus, in a two-inlet port to one-outlet port arrangement, the working area of the chamber which confines the cells and medium can be maintained in a constant shape to optimize fluid flow and provide even flow over the cells for optimal cell growth. More specifically, with the two-inlet to one-outlet configuration, a preferred chamber configuration includes a first portion to which the medium is introduced and a second portion to which the introduced medium flows through to reach the outlet port. The second portion preferably has a shape generally corresponding to one half of an ellipse although other shapes allowing optimal fluid flow (see FIG. 18) will be apparent to those of skill in the art.

According to another aspect of the invention, the bioreactor can be provided with a reduced volume space to start the culture which is especially advantageous when expanding stroma-free stem cell cultures. When dealing with stroma-free stem cells, there is a minimum inoculation cell density required to facilitate stem cell expansion without the use of a basal layer of stromal cells or an inert matrix or mesh. Applicants have found that this inoculation density is at least about 5,000 and preferably at least about 7,000 (BM about 7–20,000/mL; MPB about 20–50,000/mL) stem cells/mL. In one aspect, the bioreactor is provided with a depression or recess in the bottom surface of the housing that faces and defines the chamber in the upstream portion of the chamber which forms a container of a volume of about 30 mL. This depression allows for the initial placement of the cells in a reduced space of the chamber or small area of the chamber so that the initial inoculation density facilitates expansion without the use of stromal cells or basement matrix and thereby forming a local increase in cell concentration.

According to a further aspect of the invention, a head space is preferably incorporated into the bioreactor. This is generally accomplished by providing the chamber in the bioreactor with a volume that is substantially greater than the liquid volume containing the cells. According to this embodiment, the wall of the bioreactor that forms or defines the bottom of the chamber is gas impermeable and a filter is provided in the bioreactor housing to provide the free exchange of gases between the headspace portion of the chamber and the gases directly outside of the bioreactor. The filter (generally having a pore size less than or equal to 0.22 μm) is sized such that bacteria and mold spores cannot pass through but gases can. With this construction, the gas head space above the surface of the cells and can provide oxygen to the cells by diffusion through the medium.

Figure 9:
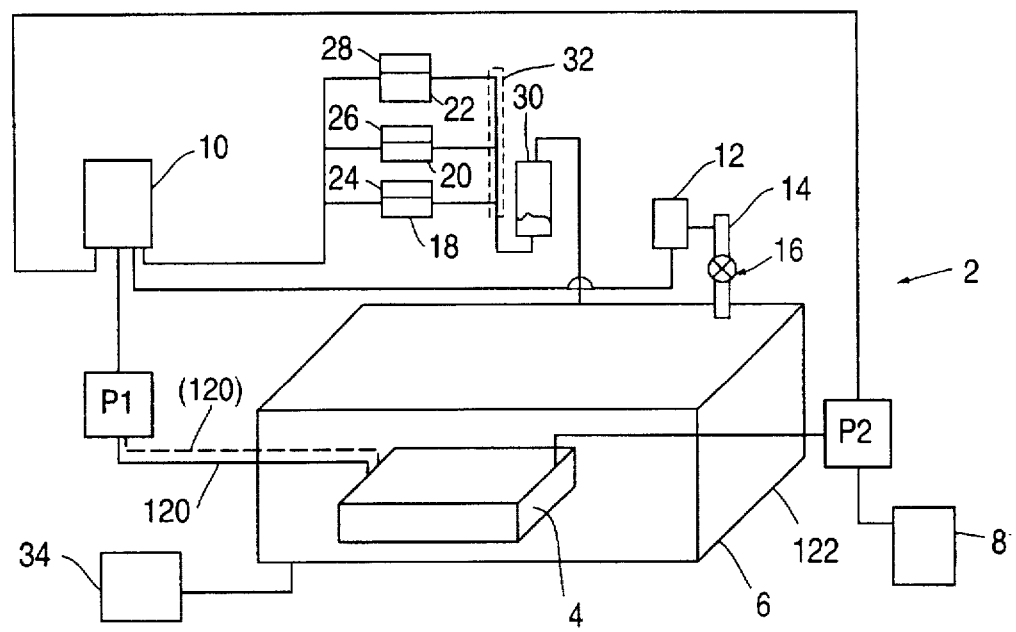
FIG. 9 is a schematic representation of the bioreactor system constructed according to the principles of the present invention.

With respect to the bioreactors of this invention and referring to FIG. 9, a bioreactor system (1) is schematically shown where feed medium is continuously added to the bioreactor in the upstream portion of the bioreactor and waste products removed from the downstream portion without removing the cells. This is accomplished because the fluid forces are less than gravitational forces on the cells. Bioreactor system (1) generally comprises bioreactor system (2) and an environmental control box (4) which surrounds the bioreactor. The system further includes a medium reservoir and pump 106 fluidly coupled to the bioreactor for delivering medium thereto. The medium sourcing pump can comprise a multi-channel syringe pump such as made by Harvard Apparatus (South Natick, Mass.) or a peristaltic pump such as a Watson-Marlow pump (Wilmington, Mass.). The former is preferred when using smaller volumes. These pumps can be provided with R232 or analog (4–20 mA)communications for connecting to a processor 8 so that the processor can control the delivery of medium to the bioreactor. Receptacle 10 is fluidly coupled to the downstream portion of the bioreactor for receiving waste products. In the head space arrangement, which will be discussed in more detail below, a suction pump 12 is provided in the discharge circuit for withdrawing fluid from the bioreactor and sending it to receptacle 10.

Bioreactor system 1 further includes a gas control system for sensing the gas content in box 4, comparing the sensed values to preselected values and delivering appropriate gases to the interior of environment control box 4 in response to deviations beyond a given value from the desired gas mixture or changes in the gas concentrations as predetermined by the process controller. In one embodiment, the control system can include a paramagnetic sensor for sensing the oxygen composition in the box and conventional infrared technology to measure the $CO_2$. These sensing systems are generally designated with reference to numeral 14 and are of conventional construction and coupled to the interior of the box as would be apparent to one of ordinary skill. These sensors are coupled to processor 8 which compares the sensed values to preset values and sends signals to mass flow control meters 16, 18 and 20 when the content of a particular constituent varies from the preselected amount by a value of 0.5%. Mass control flow controllers 16, 18 and 20 are coupled to $CO_2$, air and nitrogen sources 22, 24 and 26, respectively. The outlets of the flow meters are fluidly coupled to humidifier 28 after being mixed in chamber 30 to provide the gas mixture to be introduced into the environment control box to have a humidity slightly above about 95% of saturation.

The bioreactor system further is provided with a purge valve 32, which is a conventional one-way valve that allows gas to pass from the control box to the outside when there are gases flowing through the inlet to the control box. In general, this occurs when there is a positive pressure difference between the box and the outside. However, because pressure is not measured, it is unknown how small a pressure difference will allow gas to pass.

The system also has a conventional heating arrangement to maintain the control box at about 37° C.

Referring to FIG. 9, a cell expansion or bioreactor system 2 is schematically shown according to the present invention. Bioreactor system 2 generally comprises an expansion device or bioreactor 4 and an environment control box or incubator 6 which surrounds the bioreactor and controls the gas mixture and temperature to which the bioreactor and cells placed therein are exposed as will be described in more detail below. In general, cells to be expanded are placed in the bioreactor and feed medium continuously added to the bioreactor via pump P1 and withdrawn therefrom via pump P2 which, in turn, sends the withdrawn fluid (e.g., waste products) to a receptacle 8. This is done without removing the cells from the bioreactor and without contacting the medium around the cells; and thus, avoids the risk of contamination that may occur in other systems that require manual cell manipulation. Bioreactor system 2 facilitates a closed, continuous expansion process.

Figure 10:
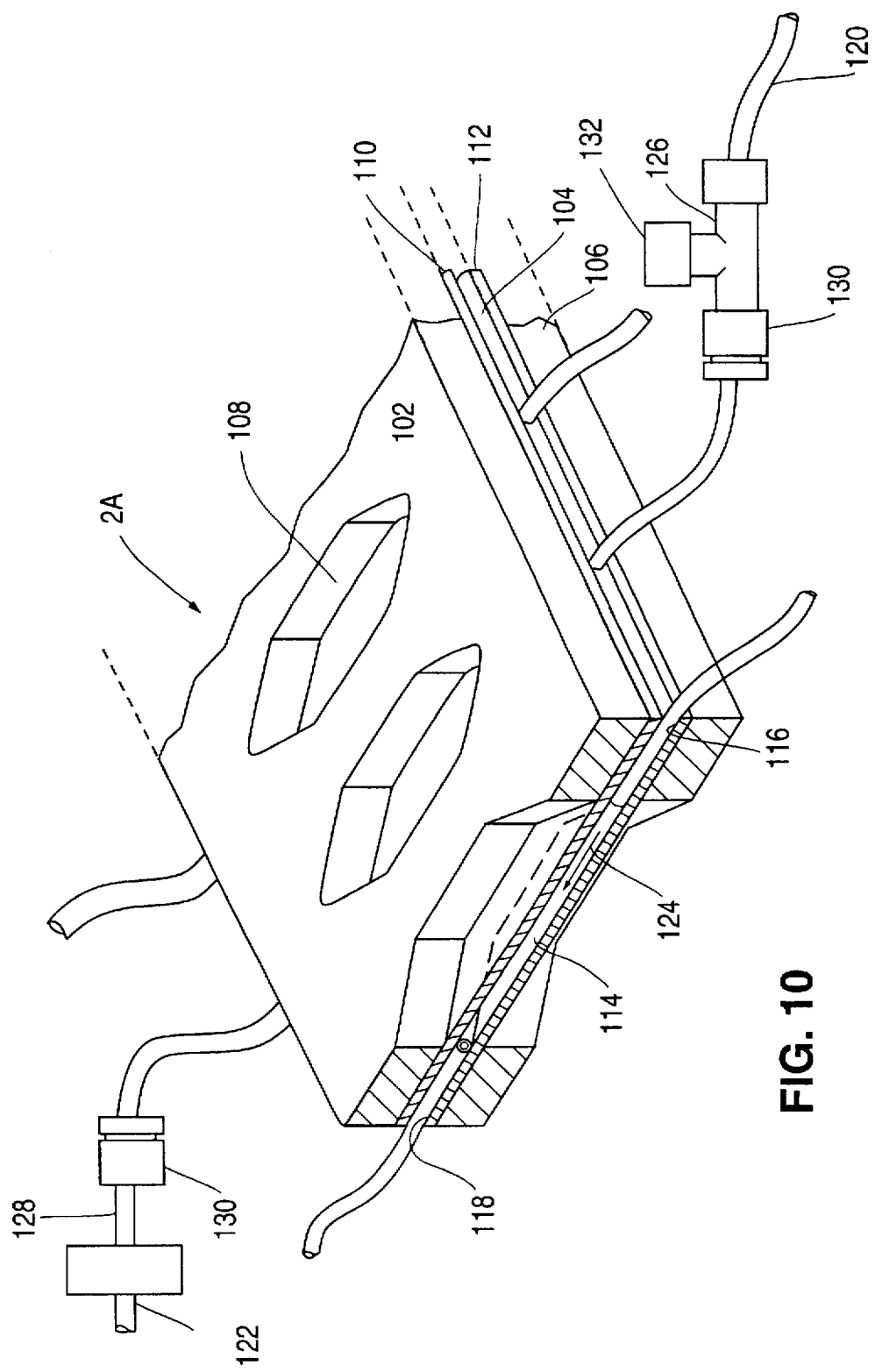
FIG. 10 is a perspective sectional view at one embodiment of a bioreactor which can be used to carry out the process of the present invention.

Referring to FIG. 10, a first embodiment of the bioreactor for facilitating cell expansion according to the present invention is shown in partial section and generally designated with reference numeral 2A. Bioreactor 2A comprises a rigid housing that includes upper, lower and middle block or support members 102, 104 and 106, respectively. The upper and lower block members can be of any suitable rigid, preferably autoclavable, material, such as aluminum. The middle block member can be silicon rubber, for example, so that its more complex configuration can be readily molded. The upper and lower block members are tightly secured to one another, such as by fasteners (not shown) that extend through the entire thickness of the bioreactor, with the middle block member and a pair of membranes sandwiched therebetween as shown in FIG. 10. The upper and lower block members rigidly support the middle block member and prevent flexure thereof, thereby facilitating forming and maintaining a constant dimension sealed expansion chamber which is described in more detail below.

Each block member has an opening 108 formed therein that is aligned with openings in the other block members when the block members are stacked in an assembled state as shown in FIG. 10. Laminae or membranes 110 and 112, each of which can be generally in the form of a film, are disposed between upper and middle block members 102, 104 and middle and lower block members 104, 106. In this manner, middle block member 104 and the portions of film members 110 and 112 that extend over a respective opening 8 in middle block member 104 form an expansion chamber 114. At least one of the film members 110 and 112 preferably are gas permeable to facilitate the exchange of gases (e.g., oxygen, carbon dioxide and nitrogen) between the expansion chamber and the interior of environment control box 6 and the expansion chamber(s). On the other hand, they should be water impermeable to prevent the medium or cells in the expansion chamber(s) from passing therethrough. One suitable film member material is Teflon® (FEP) having a thickness in a range of 0.002 to 0.020 inches. Although three expansion chambers are shown, it should be understood that any number of expansion chambers can be used creating a uni- or multi-chamber bioreactor system.

Middle block member 104 also includes an expansion container or chamber inlet and outlet port 116, 118 formed through side walls thereof and fluidly coupled to each expansion chamber as shown in FIG. 10. These ports can be integrally formed in block. For example, silicone molded member 104 has members 116 and 118 molded as part of it. In this manner, feed and discharge conduits or lines 120, 122 can be fluidly coupled to the expansion chambers. In this case, these ports can be formed to include tubular portions that extend beyond the upper and lower block members to simplify their coupling to feed and discharge conduits or lines 120 and 122. Feed and discharge lines 120 and 122, in turn, are coupled to pumps P1 and P2, respectively, so that medium can be flowed through the conduits and inlet ports and into the expansion chambers as indicated with reference arrow 124. Lines 120 and 122 also preferably are provided with conventional adapters 126 and 128, respectively, having conventional luer type connections (Value Plastic, Inc.) Inlet adapters 126 further include syringe septum or luer connection mechanisms which permit the injection of cells into expansion chamber(s) 114 via line(s) 120.

The rigid block member construction advantageously facilitates the expansion chamber dimensions to be particularly defined to facilitate uniform flow and essentially even distribution of medium over the cells. In the illustrative embodiment, openings 108 in middle block member 104 are generally hexagonal to facilitate such flow. The corresponding openings in the upper and lower block members are similarly shaped and sized to provide essentially uniform gas exchange over the entire medium surface in the expansion chambers which preferably have a volume of about 1 mL and a height of about 2 to 4 mm, preferably 3 mm.

In operation, medium is flowed into the expansion chambers via line 120 to remove any air in the lines and expansion chambers. Then, cells to be expanded are introduced into the expansion chambers via a syringe (not shown) and respective syringe septum or luer connection 132. Medium is flowed through the expansion chamber such that it remains completely filled.

The bioreactor illustrated in FIG. 10 is generally appropriate for relatively small expansion models. When larger expansion chambers are desired, such as in the case where a large expansion of cells is desired, a multiple inlet or outlet port configuration preferably is used as will be described in detail below.

Referring to FIGS. 11 to 14, another embodiment of the bioreactor of the present invention is shown and generally designated with reference numeral 28. Bioreactor 2B comprises a rigid housing 202 that defines an expansion chamber 204 having an upstream end portion 206 and a downstream end portion 208. Bioreactor 2B may have a laminate or sandwich construction that comprises, from top to bottom, upper block member 210, gas permeable 212 (which can be Teflon® or other well known tissue culture compatible materials, with about a 0.005 inch thickness), gasket 214, mesh sheet 216 and lower block member 218. Impermeable materials can be used with a headspace, such as polystyrene or polycarbonate. The upper and lower block members are preferably rigid and are tightly secured together such as by fasteners (not shown) through the entire thickness of the bioreactor to rigidly constrain the laminate construction and seal the expansion chamber.

Upper block member has a recess formed therein which together with membrane 212 forms cell expansion chamber 204. Upper block member 210 can be, for example, polycarbonate, polysulfone or polystyrene and preferably is transparent to facilitate viewing cells in the expansion chamber. Polycarbonate is preferred when the unit it is to autoclaved. Gasket 214 provides a seal between membrane 212 and lower block member 218 and can be of any suitable material such as silicone. Gasket 214 also forms the side walls of the bioreactor fluid chamber and as such should be a sterilizable, biocompatible material. Mesh sheet 216 rests on lower block member 218 and provides support for membrane 212 to maintain membrane 212 essentially flat. Mesh sheet 216 can be any conventional material such as polyester or nylon and preferably has a mesh size of 8×8 (8 mesh/inch) to facilitate viewing the cells in chamber 204. It should be understood that other mechanisms for supporting membrane 212 also can be used. For example, spacer pins can be formed to extend from lower block member 218 to membrane 212.

Block member 218 includes a plurality of holes 220 formed therethrough that are aligned with expansion chamber 204 to provide viewing of the chamber and allow exchange of gases between the expansion chamber and the interior of environment control box 6 when the bioreactor is positioned upside down (i.e., in a cell expansion start mode). Lower member 218, which includes a recessed portion in which holes 220 are formed (see the same element in the embodiment of FIG. 15) so that a microscope can be more closely placed near membrane 212, can be plastic or aluminum.

An important aspect of this embodiment is that the bioreactor further includes multiple inlet or outlet ports for the expansion chamber. These ports are in the vicinity of the upstream and downstream end portions and are in fluid communication with the chamber. The number of ports in the vicinity of one of the upstream and downstream portions is greater than the number of ports in the vicinity of the other one of those portions. With this construction, a compact bioreactor that facilitates uniform flow over cells placed therein can be provided. More specifically, the multiple inlet port per outlet port (or vice versa) configuration minimizes or eliminates a possibility of channeling the medium flow through the chamber. Otherwise, there would be dead spaces in the reactor where cells may not receive any or sufficient fresh medium for proper cell growth. This is especially the case when dealing with expansion chamber volumes of greater than about 2 mL.

In a preferred embodiment, the bioreactor has two inlet ports 222 fluidly coupled to pump P1 (FIG. 9) for providing medium in the upstream portion of the bioreactor chamber and one outlet port 224 fluidly coupled to pump P2 (FIG. 9) arranged for discharging medium from the downstream portion of the chamber as shown in FIGS. 11 and 12, for example. This configuration allows a more compact design than a single input to single output which would be substantially longer and thinner to get good fluid distribution and thus more difficult to handle in a laboratory or clinical environment.

Figure 13:
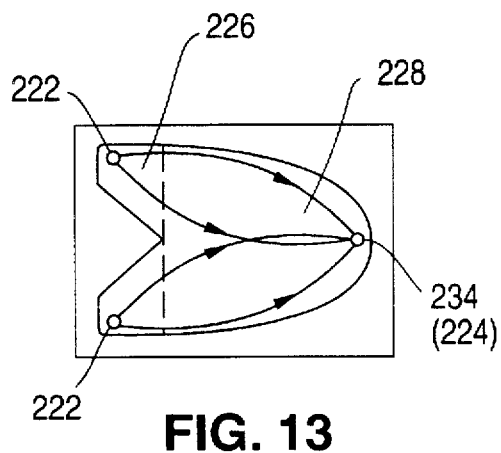
FIG. 13 schematically illustrates the medium flow pattern in the bioreactor expansion chamber of FIG. 11.
Figure 14:
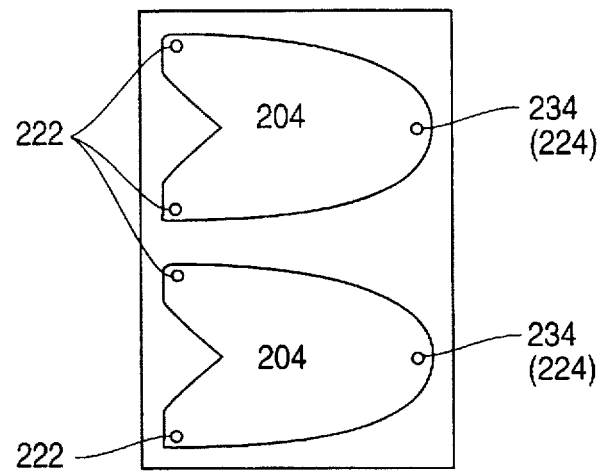
FIG. 14 schematically illustrates the bioreactor shown in FIGS. 11 to 13 in a multiple expansion configuration.

The rigid feature (which also can be provided by a gas permeable bag) of the bioreactor also advantageously facilitates providing a constant chamber configuration that will provide optimal fluid flow therethrough for any given number of inlet and outlet ports. Thus, in a two-inlet port to one-outlet port arrangement, the working area of the chamber which confines the cells and medium can be maintained in a constant shape to optimize fluid flow and provide even flow over the cells for optimal cell growth. More specifically, with the two-inlet to one-outlet configuration, a preferred chamber configuration includes a first portion 226 to which the medium is introduced and a second portion 228 to which the introduced medium flows through to reach the outlet port as schematically shown in FIG. 13 together with the general resultant flow patterns. The second portion can have a shape generally corresponding to one half of an ellipse. It should be understood that when other inlet/outlet port arrangements are used, other expansion chamber configurations may provide optimal fluid flow. In addition, although bioreactor 2B is shown with a single expansion chamber, it can be constructed with multiple expansion chambers as schematically shown in FIG. 14.

In use, bioreactor 2A is initially positioned upside down with the gas permeable side up (the lower block member up) and the cells resting on the gas impermeable surface until the cell density reaches a threshold density (e.g., $10^5$ cells/mL) on day 7 to 10, when the bioreactor is flipped.

There is evidence to suggest that oxygen radicals, when coming in contact with stem cells, cause the cells to differentiate or die as opposed to expanding clonally. It was determined that using the sandwich bioreactor construction described above (FIGS. 11 to 14) with one gas permeable and one gas impermeable membrane and then starting the bioreactor with the gas impermeable side down alleviates some of these problems. (See FIGS. 1 and 8). With this configuration oxygen radicals must permeate the gas-permeable membrane and diffuse through the liquid layer before reaching the cells, such that there is a strong probability that the oxygen radicals will come in contact with an oxygen radical scavenger in the medium before reaching the cells. Whereas with the gas permeable side down, the oxygen radicals can contact the cells directly from below without having to travel through much of the medium.

To improve bioreactor performance, a headspace system can be used. This system has a gas impermeable bottom membrane with a gas headspace above the surface for gas transfer to the cells. Unlike the sandwich design that uses either two gas permeable or one gas permeable and one gas impermeable membrane and therefore needs to be "flipped" to keep the culture expanding, the headspace system requires no such orientation shifting. It should be noted that the headspace system can optionally expand progenitors or up to $5 \times 10^6$ cells/mL.

Figure 15:
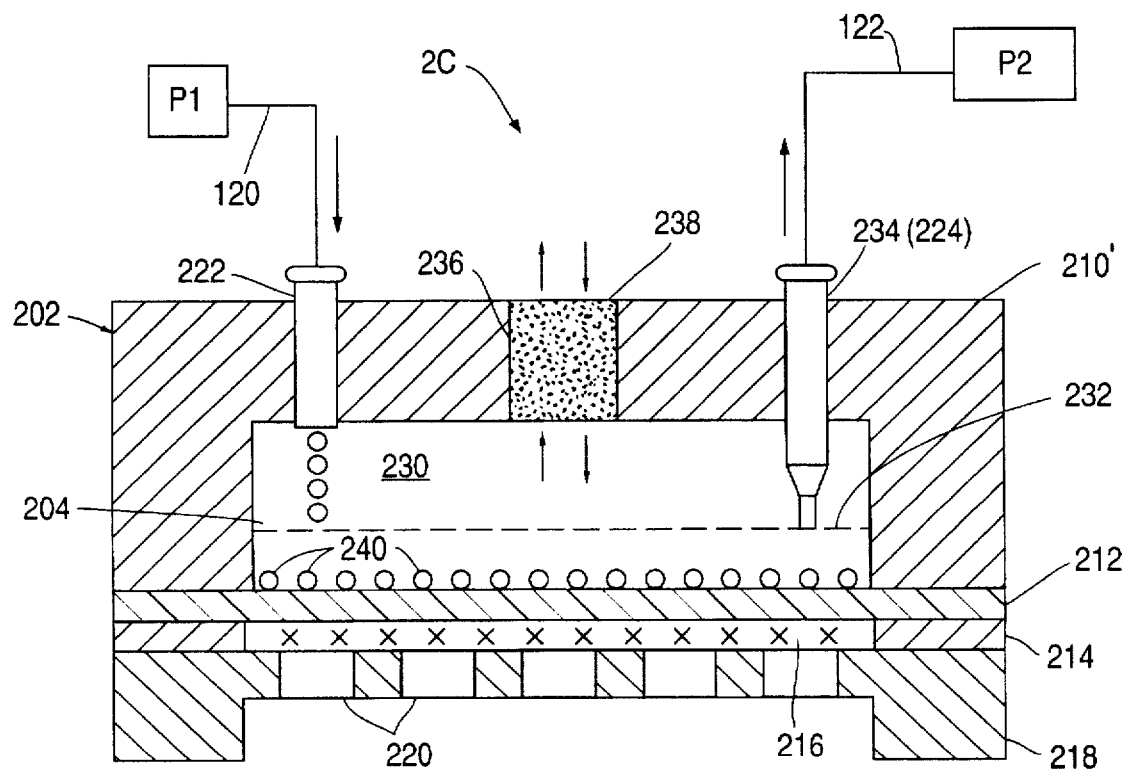
FIG. 15 is a transverse section of yet a further bioreactor of the present invention illustrating a headspace system.

Referring to FIG. 15, a headspace bioreactor configuration is shown according to the principles of the present invention and generally designated with reference numeral 2C. Bioreactor 2C is the same as bioreactor 2B with the exception of having a larger expansion chamber (to accommodate a headspace 230 above medium line 232), a dip tube 234 which preferably forms the outlet port (or vice versa) to control volume of medium in the chamber and a vent or through hole 236 in upper block member 210 to facilitate the exchange of gases between expansion chamber and the interior of the environment control box 6. As would be apparent to one of ordinary skill, tube 234, which can have a pipette tip configuration at its distal end, can be raised or lowered to control the level of the medium in the expansion chamber. For a 30 mL liquid volume, the headspace preferably is in the range of about 60 to 200 mL in volume. With the headspace system, membrane 212, which supports cells 240 can be gas impermeable because the headspace will be in gas exchange with the environment directly outside the bioreactor. Vent hole 236 preferably has a filter, such as a 0.22 micron filter, disposed therein to substantially maintain the sterile environment in the expansion chamber. To maintain a constant height of medium when medium is being introduced, pump P2 is set to withdraw fluid at a slightly greater flow rate (e.g., about 105% of the outlet flow rate) so that the outlet pump will withdraw both liquid and air. (As is known to those of skill in the art, flow rate=(perfustion rate)×(liquid volume)). This works because the outlet pump will only draw liquid when the liquid level reaches the dip tube thereby maintaining the liquid level at the dip tube opening. The medium height is then determined by the immersion depth of the dip tube 234.

Figure 16A:
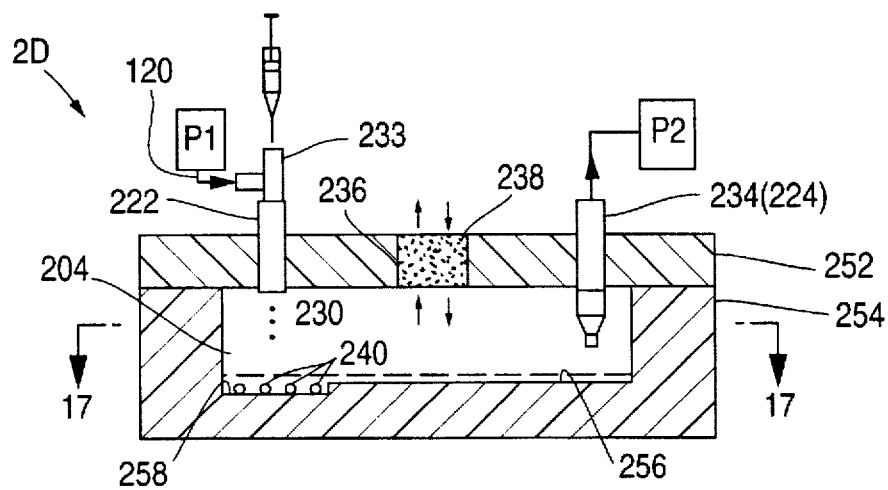
FIGS. 16A and 16B are cross-sections of yet another bioreactor embodiment constructed according to the principles of the present invention.
Figure 16B:
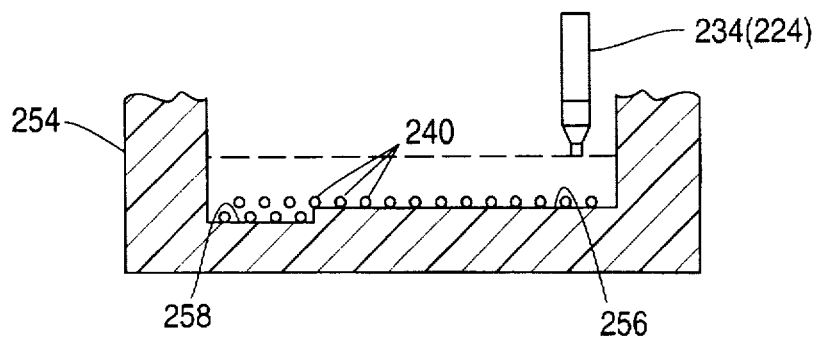
Figure 17:
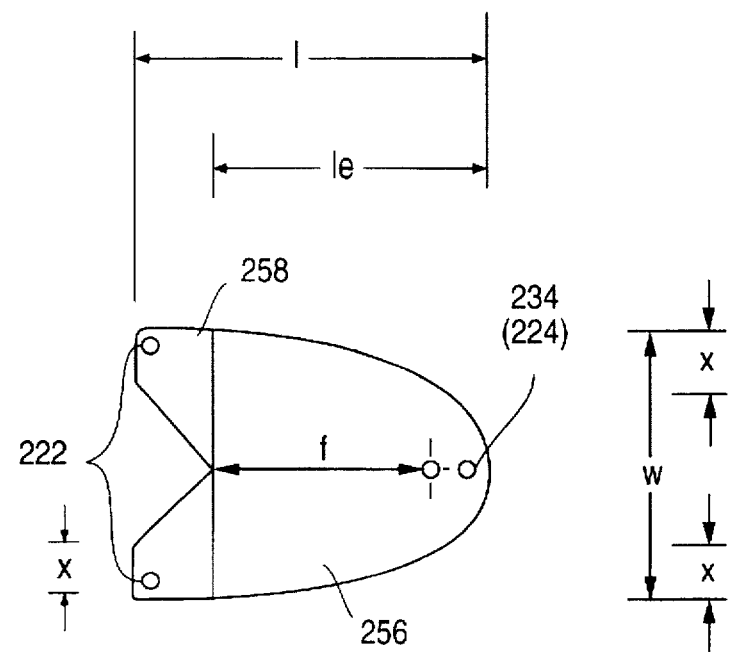
FIG. 17 is a sectional view of the bioreactor of FIG. 16A taken along line 17—17.

Referring to FIGS. 16A, 16B and 17, a further and most preferred embodiment of the bioreactor of the present invention is shown. According to this embodiment of the invention, the bioreactor is provided with a reduced volume space to start the culture which is especially advantageous when expanding stroma-free stem cell cultures. When dealing with stroma-free stem cells, there is a minimum inoculation density to produce the requisite number of $CD34^+$ cells. Applicants have found that this number is at least about 5,000 and preferably at least 7,000 cells/mL (BM 7–20,000 cells/mL; MPB 20–50,000 cells/mL).

Referring to FIG. 16A, bioreactor 2D comprises a rigid housing that includes an upper block member 252 and a lower block member 254. Both of these members preferably are plastic and can be polycarbonate, polystyrene or polysulfone as discussed with respect to upper block member 210. Preferably, they are transparent to facilitate observation of the cells in the expansion chamber. The upper and lower block members may be, for example, RF or ultrasonically welded together.

Lower block member 254 is provided with multiple recesses or depressions to provide a variable volume chamber with a reduced volume starting space. In the illustrative embodiment, the upper wall of the lower block member that faces expansion chamber 204 has a stepped surface. This surface includes a first surface 256 and a second lower or deeper surface 258 that define first and second recesses in the lower block member. The latter forms the initial reduced space for the expansion cells. The second surface 258 preferably constitutes about 10–20% of the combined first and second lower block member bottom surfaces and forms a recess with a depth of about 2 mm. This depression allows for the initial placement of the cells in a reduced space of the chamber or small area of the chamber so that they can pack closer together to start and thereby form a local increase in cell concentration. Bioreactor 2D also preferably has multiple port configuration (as shown in FIG. 13, one inlet port being hidden from view in FIG. 16A) and expansion chamber shape as that shown in FIG. 13 and the headspace arrangement as shown in FIG. 15. That is, the preferred inlet/out port configuration and chamber shape is the same as in headspace bioreactor 2C.

Cells can be initially placed in bioreactors 2B, 2C and 2D by using a T-fitting 233 (FIG. 16A). Each t-fitting 233 has one branch fluidly coupled to a respective feed conduit 120 from pump P1. The second branch of each T-fitting is coupled to a respective inlet port 222 and the third branch of the T-fitting is provided with a septum that facilitates introduction of feed cells therethrough with a syringe.

The following dimensions for a 30 mL liquid expansion volume chamber (where the 30 mL can be the volume of the space bounded by surface 258 and the plane with which surface 256 is coplanar) are provided for purposes of example only and with reference to bioreactor 2D and FIGS. 16B and 17. This example is not intended to limit the invention. For an expansion chamber having an overall length (l) of 1.71 inches, le (length of ½ ellipse surface (surface 256) of 1.32 inch), width (w) of 1.32 inches, height 0.8 inches, foci distance (f) 1.14 inches and dimension of 0.26 inches, a headspace (the volume above medium line 232) of about 122 mL provides suitable results.

Returning to FIG. 9, bioreactor system 2 includes a pump P1 (which includes a medium reservoir) fluidly coupled to the bioreactor for delivering medium thereto. Pump P1 can comprise a multi-channel syringe pump such as made by Harvard Apparatus (South Natick, Mass.) or a peristaltic pump such as a Watson-Marlow pump (Wilmington, Mass.). The former pump system is desirable for very accurate delivery of medium at relatively small flow rates (e.g., 0.1 mL per day). The latter system is preferred for larger flow rates (e.g., 20 mL per day). These pumps are available with RS-232 ports for connecting to a processor 10 so that the processor can control the delivery of medium to the bioreactor which can be through a single or multiple conduits (e.g., conduits 120) to single or multiple inlet ports as discussed above. Receptacle 8 is fluidly coupled to the downstream portion of the bioreactor for receiving waste products. In the headspace arrangement, a suction or peristaltic pump 12 is provided in the discharge line(s) for withdrawing fluid from the bioreactor and sending it to receptacle 8. The flow rates of pumps P1 and P2 can be controlled by processor 10 which is programmed with preselected flow rates for various time intervals in an expansion cycle.

Bioreactor system 2 further includes a gas control system for sensing the gas content in environment control box 4, comparing the sensed values to preselected values and delivering appropriate gas to the interior of environment control box 4 in response to deviations beyond a given value from the desired gas mixture. A starting composition of 5% $CO_2$, 5 to 20% $O_2$, balance—$N_2$ gas, mixture is preferred. The processor is set to maintain these values with an allowable 0.5% deviation by triggering the addition of $CO_2$, $N_2$ or air as required.

In one embodiment, the control system can include a paramagnetic sensor for sensing the oxygen composition in the box and conventional infrared technology to measure the $CO_2$. These sensing systems are schematically shown and generally designated with reference to numeral 12 and are of conventional construction. They are coupled to the exhaust stack 14 of one-way valve assembly 16 which is fluidly coupled to the interior of incubator 6. The one-way valve will to purge gas from the environment control box when gas is supplied to box 4. These sensors are also coupled to processor 10 which compares the sensed values to preset values (discussed above) and sends signals to mass flow control meters 18, 20 and 22 when the content of a particular constituent varies from the preselected amount by a value of 0.5%. Mass control flow meters 18, 20 and 22 are coupled to $CO_2$, air and nitrogen sources 24, 26 and 28, respectively. The outlets of the flow meters are fluidly coupled to a humidifier 30 after being mixed in chamber 32 to provide the gas mixture to be introduced into the environment control box to have a humidity preferably slightly above about 95% of saturation. The system also has a conventional heating arrangement to maintain the control box at about 37° C.

The particular time period for moving from initial oxygen concentrations to the increased oxygen concentrations can be programmed into the process. The time period (e.g., 7 to 10 days time) will depend on the following factors: a) initial cell concentration, b) initial cell "type" composition, c) cytokines added to the culture, and d) cell or tissue source (BM or MPB). The exact time when the gas volume is changed is empirically determined for a set of the above factores and then used to program a present time in the processor at which gas content is changed for expansion of cells where the set of factors applies.

It is further contemplated that in addition to controlling medium flow rates and gas composition in the incubator, the processor estimates the cell number based on previously collected data. It is also contemplated that the processor monitors the amount of medium (based on material balances) in the receptacle, feed source and the bioreactor itself and changes the color of the corresponding image of each of those items to graphically represent its volume.

The following examples are set forth to illustrate, but not limit the invention.

Experimental Examples

Materials and Methods

Medium and Cytokines. Cell culture medium that was used was either IMDM or SSP10, supplemented with 10% fetal bovine serum, $10^{-5}$M 2-mercaptoethanol, 50µg/mL streptomycin, 50 U/mL penicillin and cytokines. Cytokines used for cell culture or for the culture of the methylcellulose assay were: recombinant human (rh) IL-3 (Sandoz) and rhIL-6 (Sandoz), rh GM-CSF (Immunex), and rh Epogen (Amgen), rh c-kit ligand (R and D Systems) and G-CSF (Amgen).

Cell Isolation. Sorted CD34$^+$Thy1$^+$Lin$^-$ cells from either adult bone marrow (ABM) or mobilized peripheral blood (MPB) were used for each experiment. The culture conditions varied with each experiment as described in the separate examples.

For ABM, fresh 20 mL of bone marrow was isolated by aspiration of the iliac crest from human normal volunteers from Stanford University Medical Center (Palo Alto, Calif.) or Scripps Research Institute (La Jolla Calif.). Marrow was separated by taking the mononuclear cell fraction following a Ficoll-Perque separation, positive-selected for CD34$^+$ cells according to the method described by Sutherland et al. (1992) *Exp. Hematol*.20:590. Briefly, cells were resuspended in staining buffer (SB) (HBSS containing 10 mM HEPES, 2% heat-inactivated FCS) at 5×10$^7$ cells/mL. QBEND10 (anti-CD34) (Amac, Westbrook, Me.) was added at 1/100 dilution, and cells incubated on ice for 30 minutes. Cells were then washed in SB with a FCS underlay, and resuspended at 4×10$^7$/mL in SB. An equal volume of washed Dynal sheep anti-mouse IgG$_1$Fc magnetic beads (Dynal, Oslo, Norway), was added at a 1:1 bead to cell ratio, to give a final cell concentration of 2×10$^7$ cells/mL. After 30 min incubation on ice, with gentle inversion, the tube was placed against a Dynal magnet (Dynal) for 2 minutes, and CD34$^-$ cells removed. Following two washes, 20 µL of 'glycoprotease' (O-sialoglycoprotein endopeptidase, Accurate Chemical, Westbury, N.Y.) plus 180 µL of RPMI (JRH Biosciences)/20% FCS were added and the beads incubated at 37° C. for 30 minutes to cleave the QBEND10 epitope, and release CD34$^+$ cells from the beads. Beads were then washed three times to maximize cell recovery. The glycoprotease used for the release step in the positive selection procedure has been shown not to effect subsequent ex vivo expansion of progenitors. Marsh et al. (1992) *Leukemia* 6:926.

Mobilized peripheral blood (MPB) samples were obtained with informed consent from multiple myeloma patients treated at the University of Arkansas Medical Center. The patients were treated on day 1 with cyclophosphamide at 6 g/m$^2$ (1.5 g/m$^2$ every 3 hours×4 doses). From day 1 until the start of leukopheresis (usually 10–28 days), granulocyte macrophage colony stimulating factor (GM-CSF) was given at 0.25 mg/m2/day. Apheresis for total white cells was started when the peripheral blood white cell count was greater than 500 cells/µl and the platelet count was greater than 50,000 cells/µl. Patients were apheresed daily until from 6×10$^8$ mononuclear cells (MNC) were collected.

Fresh MPB samples were elutriated with a JE5.0 Beckman counterflow elutriator equipped with a Sanderson chamber (Beckman, Palo Alto, Calif.). Cells were resuspended in elutriation medium (Biowhittaker, Walkersville, Md.) at pH 7.2, supplemented with 0.5% human serum albumin (HSA). The rotor speed was set at 2000 RPM, the cells were introduced, and the first fraction collected at a flow rate of 9.6 mL/min. Fractions 2 and 3 were collected at the respective flow rates of 14 and 16 mL/min. The larger cells remaining in the chamber were collected after stopping the rotor. Cells were resuspended in RPMI supplemented with 5% HSA, 10 µg/mL DNAse I and penicillin/streptomycin at 50 U/mL and 50 µg/mL, respectively. Fractions 2 and 3 were pooled and incubated with 1 mg/mL heat-inactivated human gamma-globulin to block non-specific Fc binding. Granulocytes were further depleted by incubation with CD15 conjugated to magnetic beads (Dynal M450, Oslo, Norway) followed by magnetic selection.

CD34$^+$Thy1$^+$LIN$^-$ cells ("Thy$^+$") were isolated from AMB and MPB by flow cytometry as follows. Antibodies to CD14 and CD15 were obtained as FITC conjugates from Becton-Dickinson. Antibody to Thy-1 (GM201) was obtained from Dr. Wolfgang Rettig (Ludwig Institute, New York), and was detected with anti-y1-PE conjugate from Caltag. Antibody to CD34(Tük 3) was obtained from Dr. Andreas Ziegler (University of Berlin), and detected with an anti-y3-Texas Red conjugate (Southern Biotechnologies).

Anti-CD34 antibody or an IgG3 isotype matched control were added to cells in staining buffer (HBSS, 2% FCS, 10 mM HEPES) for 20 minutes on ice, together with anti-Thy-1 antibody at 5 µg/mL. Cells were washed with a FCS underlay, and then incubated with Texas Red conjugated goat anti-mouse IgG3 antibody and phycoerythrin-conjugated goat anti-mouse IgG1 antibody for 20 minutes on ice. Blocking IgG1 was then added for 10 minutes. After blocking, the FITC-conjugated lineage antibody panel (CD14 and CD15) was added, and incubated for another 20 minutes on ice. After a final washing, cells were resuspended in staining buffer containing propidium iodide (PI).

Cells were sorted on a Vantage cell sorter (Becton Dickinson) equipped with dual argon ion lasers, the primary laser emitting at 488 nm and a dye laser (Rhodamine 6G) emitting at 600 nm (Coherent Innova 90, Santa Cruz, Calif.) or on a high speed cell sorter as described in PCT patent application number PCT/US93/08205. Residual erythrocytes, debris and dead cells were excluded by light scatter gating plus an FL3 (PI) low gate. The sorted cell population was diluted 1:1 in HBSS, pelleted, and resuspended in HBSS for hemocytometer counting. In some experiments, the CD34$^+$LIN$^-$Thy$^-$ ("Thy$^-$") cells were also sorted and expanded as described in separate examples.

Culture Systems. Thy-1$^+$ cells isolated by the method described above were placed in bioreactors of either 1 mL or 30 mL total volume. Bioreactors were run similarly to the methods described for plate culture by Srour et al. (1993) *Blood* 81:661. The bioreactors were inoculated at densities between 7000–20,000 cells/mL, fed by medium perfusion starting day 10. Stroma-free medium contained 10 g/mL IL-3, 10 ng/mL IL-6, 10 ng/mL GM-CSF, and 50 ng/mL c-kit ligand except where otherwise noted. Cytokines were replenished every 48 hours starting on day 4. Large scale bioreactors were run under "variable volume" operation such that the reactor volume was increased during expansion. The immunophenotype of expanded cells was determined by flow cytometry.

Mobilized blood was incubated at densities between 20,000 and 50,000 cells/mL. Again, "variable volume" operation was used to increase the effective volume of the bioreactor during expansion. Medium feeding was begun on day 7; however, no cytokine replenishment was performed. Other conditions were similar to bone marrow culture as described above.

The bioreactor used had a gas permeable membrane on one side and a gas impermeable, machined polycarbonate piece of plastic on the other. Feed medium was continuously added to the bioreactor on one side and waste products removed on the other without removing the cells from the device.

Process control and data acquisition were done by the Camille 4000 system (Sagian Inc., Indianapolis, Ind.) using TG software version 1.11. Code specific for bioreactor operation can be written by one of skill in the art. Each bioreactor was surrounded by a box kept in a 37° C. incubator. Oxygen composition within each box was measured using a paramagnetic sensor oxygen and the $CO_2$ was measured using infrared technology. Oxygen, nitrogen, and carbon dioxide were metered into the bioreactor system using massflow controllers from Sierra Instruments (Monterey, Calif.) mixed by connecting the gas lines together, and humidified by passing the gas through a bubbler system. Pumps used for medium perfusion were either Watson-Marlow (Wilmington, Mass.) peristaltic pumps or Harvard Apparatus (South Natick, Mass.) syringe pumps. Pumps were controlled through a device driver written for Camile software.

Figure 8:
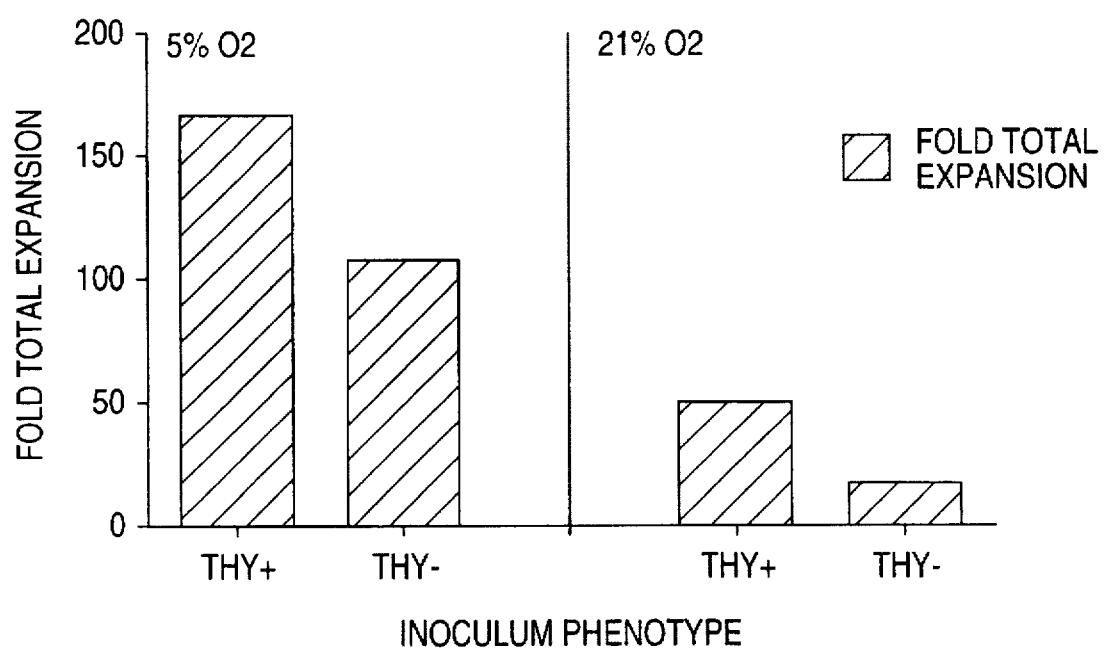
FIG. 8 is a bar graph depicting a comparison of starting oxygen concentration and inoculum phenotype on total cell expansion.

Oxygen Effects on Expansion. Oxygen was found to be a critical parameter for the growth of hematopoietic stem cells in the gas permeable membrane bioreactors. The starting oxygen concentration was tested using both Thy-1$^+$ and Thy-1$^-$ cells placed in culture. FIG. 8 shows that the total cell numbers that are produced from the expansion of Thy-1$^+$ and Thy-1$^-$ input populations are much higher under low oxygen conditions than with high oxygen. The expansion of CD34$^+$ cells showed similar trends.

However, as the cell density increased, oxygen demand increased as well. The cultures performed better if the ambient oxygen was increased, either gradually through a controlled system, or step-wise from a 5% oxygen to a 21% oxygen incubator (FIG. 1). These oxygen-controlled cultures reached higher maximal cell densities (1.6–5×10$^6$, compared to 0.8–1×10$^6$ cells/mL) after three weeks of expansion for the 3 tissues tested. Oxygen requirements of the MNC fraction have been shown to be optimal at 21% for the gas phase (Palsson (1993) *Bio/Tech.* 11:368) whereas the results presented herein show that a lower starting oxygen concentration (e.g., 5%) causes improved stem cell expansion. The reason for the difference is most likely due to the fact that the oxygen demand for a smaller, relatively homogeneous, and generally quiescent population of stem cells is much less than the oxygen demand for a large heterogenous MNC population. A high concentration of toxic oxygen radicals would make the overall performance of the culture more susceptible to radical attack, or at least more susceptible to differentiation. Other research has suggested that there is an optimum in hematopoietic progenitor expansion at low oxygen concentrations and that high oxygen directly causes blood cell differentiation of the lymphoid lineage. Ishikawa et al. (1988) *Eur. J. Haematol.* 40:126; Katahira et al. (1987) *Int. J. Cell. Clon.* 5:412; and Watanabe et al. (1993) *Eur. J. Immunol.* 23:200.

Small Scale Reactors. Thy-1$^+$ cells (CD34$^+$Thy-1$^+$LIN$^-$) were suspended at 10,000 cells/mL in SSP10 medium containing IL-3 (10 ng/mL) and c-kit ligand (50 ng/mL). One mL of the cell suspension was inoculated into each of 4 chambers (each chamber having a volume of 1 mL) of a bioreactor 2 days after inoculating. 2 of the chambers received concentrated cytokines (0.1 mL of SSP10 containing 100 µg/mL IL-3 and 500 µg/mL c-kit ligand). Concentrated cytokines were added to these 2 chambers on days 2, 4, 6, 8, 11, 13, 15, 18, and 20. The other 2 chambers received no treatment. Perfusion was started for all chambers on day 7 at a rate of 0.27 volume/day.

Figure 2:
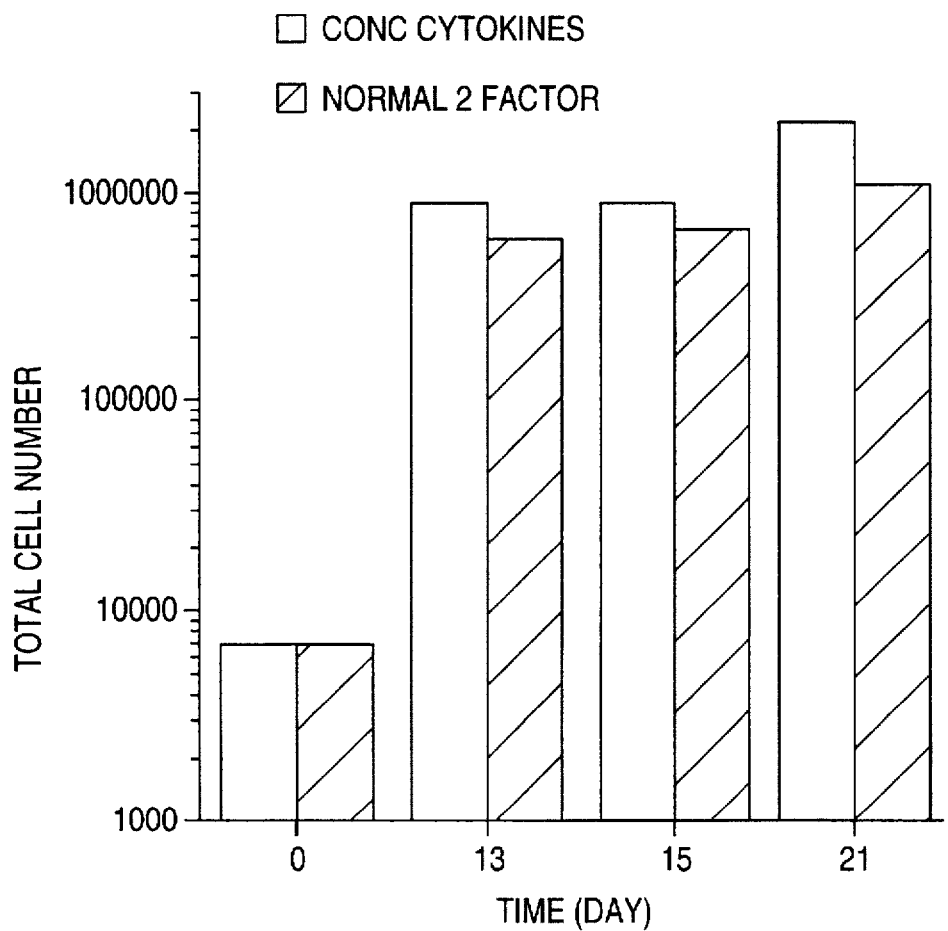
FIG. 2 shows the effect of addition of concentrated cytokines (IL-3 and c-kit (KL)) on total cell expansion from bone marrow stem cells.
Figure 3:
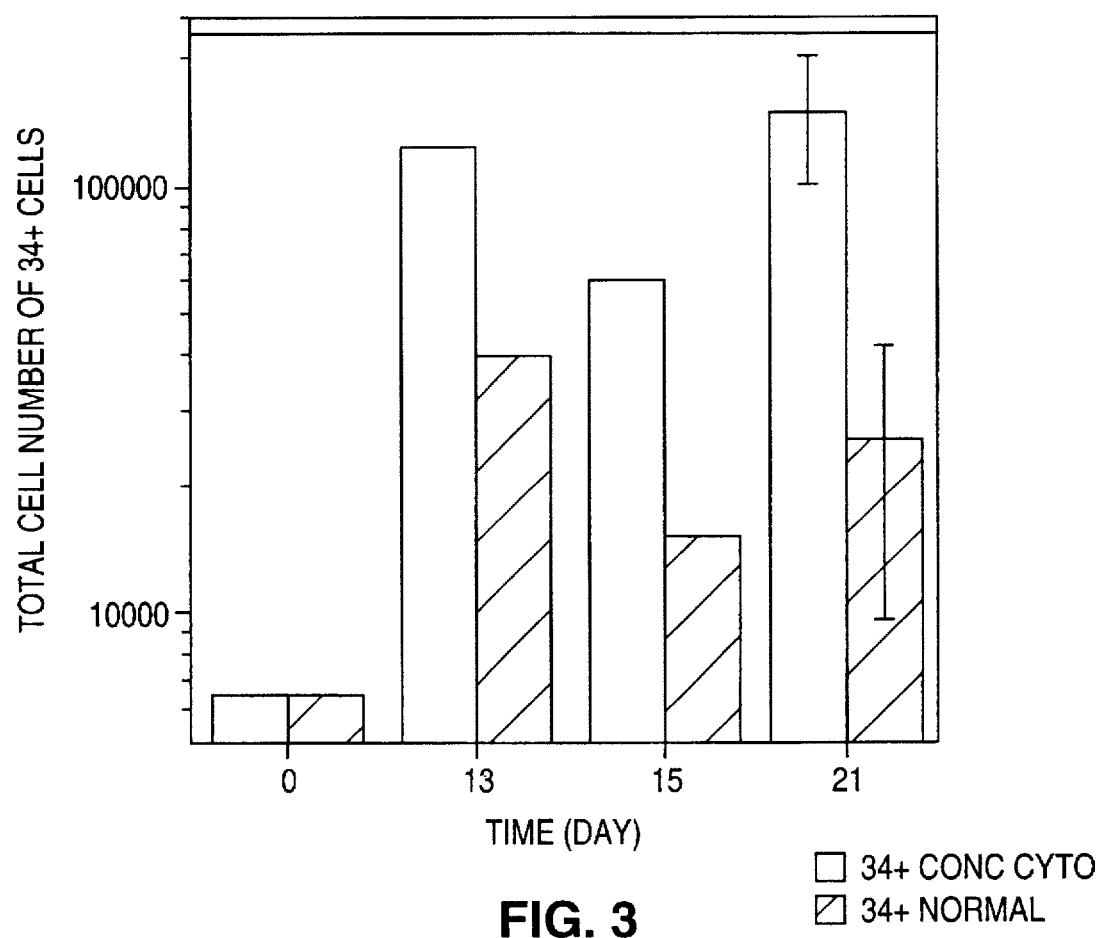
FIG. 3 shows the effect of the addition of concentrated cytokines (IL-3 and KL) on $CD34^+$ cell expansion from bone marrow stem cells.

Cells were harvested on days 13 and 15. The cells harvested on day 15 were diluted 1:3 in fresh medium. One-third of the cells were used for analysis and the other ⅔ were reseeded into new bioreactor chambers (⅓ of each old chamber for each new chamber). Perfusion was halted after reseeding, but was restated on day 18 at a rate of 0.25 volume/day. Final harvesting occurred on day 21. Results show that the use of concentrated cytokines increased both the total expansion as well as the CD34$^+$ phenotype expansion. These results can be seen in FIGS. 2 and 3.

30 mL Reactor Device. The material of construction for the bioreactor was polycarbonate although polysulfone, polystyrene or other materials would work just as well. This device was constructed with 2 inlets and 1 outlet to promote uniform fluid flow through the bioreactor and eliminate dead areas and flow channeling. FIG. 9 shows a detailed drawing of the device.

The in vivo expansion of Thy-1$^+$ cells from a low inoculation number to a large expansion product in a closed system necessitates a variable volume approach to maintain the expanding population at viable cell densities. Operation of the device started with 200,000 Thy-1$^+$ BM cells in 10 mL SSP-based medium. The device was inoculated with the gas permeable side up and the cells resting on the gas-impermeable polycarbonate.

Volume was increased on day 13 from 10 mL to 30 mL. Two days after volume increase, the reactor was "flipped" so that the cells rested on the gas permeable side. Replenishment of the cytokines in the medium was accomplished by adding concentrated cytokine medium. For this device, 1 mL of SSP10 medium with 100 ng/mL IL-3 and 500 ng/mL c-kit ligand was added on days 7, 10, 15 and 18 to replenish consumed factors.

To provide continuous feed to the reactor, fresh medium was introduced through the feed ports. Because the flow rate was not fast enough to disturb the cells along the bottom of the device, the medium addition effectively perfused the cell layers. Perfusion was started on day 17, or 4 days after increasing the volume. The bioreactor was perfused at about 0.25 volume exchange per day.

Figure 4:
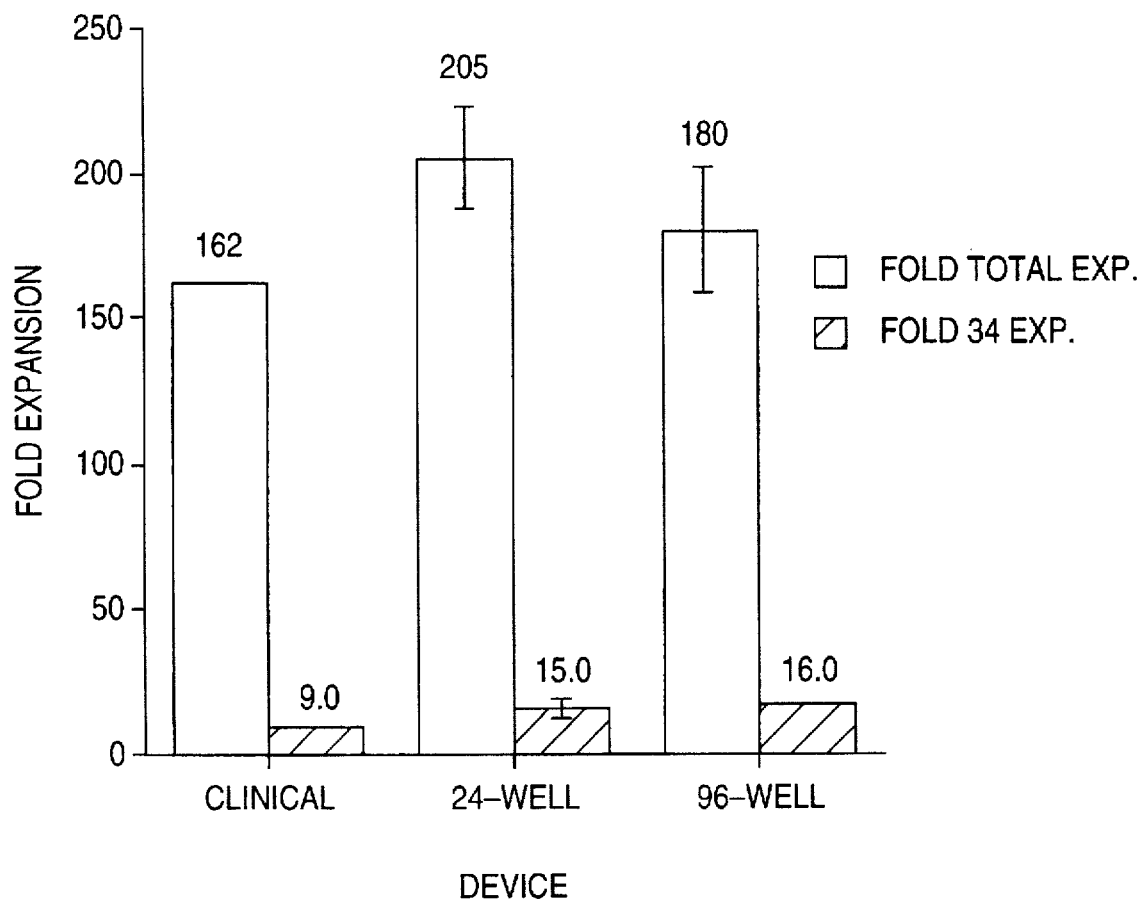
FIG. 4 shows the comparison of a clinical scale bioreactor with open culture systems for expansion of bone marrow stem cells.

The cells were harvested on day 20 and the immunophenotype was determined by flow cytometry. The results showed that for Thy$^+$ cells from bone marrow, bioreactors had similar total expansion to 24-well plates, but had less expansion of the CD34$^+$ phenotype. (See FIG. 4).

Expansion of Stem Cells Obtained From Mobilized Peripheral Blood in Bioreactors. The same bioreactor design was used for expansion of Thy-1$^+$ cells from mobilized peripheral blood as was used for the cells purified from bone marrow. The inoculum consisted of 200,000 Thy-1$^+$ cells in 10 mL of medium. The basal medium formulation was SSP10 containing IL-3 (10 ng/mL), IL-6 (10 ng/mL), G-CSF (10 ng/mL), and c-kit ligand (50 ng/mL). The 30 mL bioreactor was partially filled to 10 mL volume. After 10 days, the volume was increased to 30 mL. Perfusion was started on day 12 and continued for the remainder of the experiment. The cells were harvested on day 14.

Figure 5:
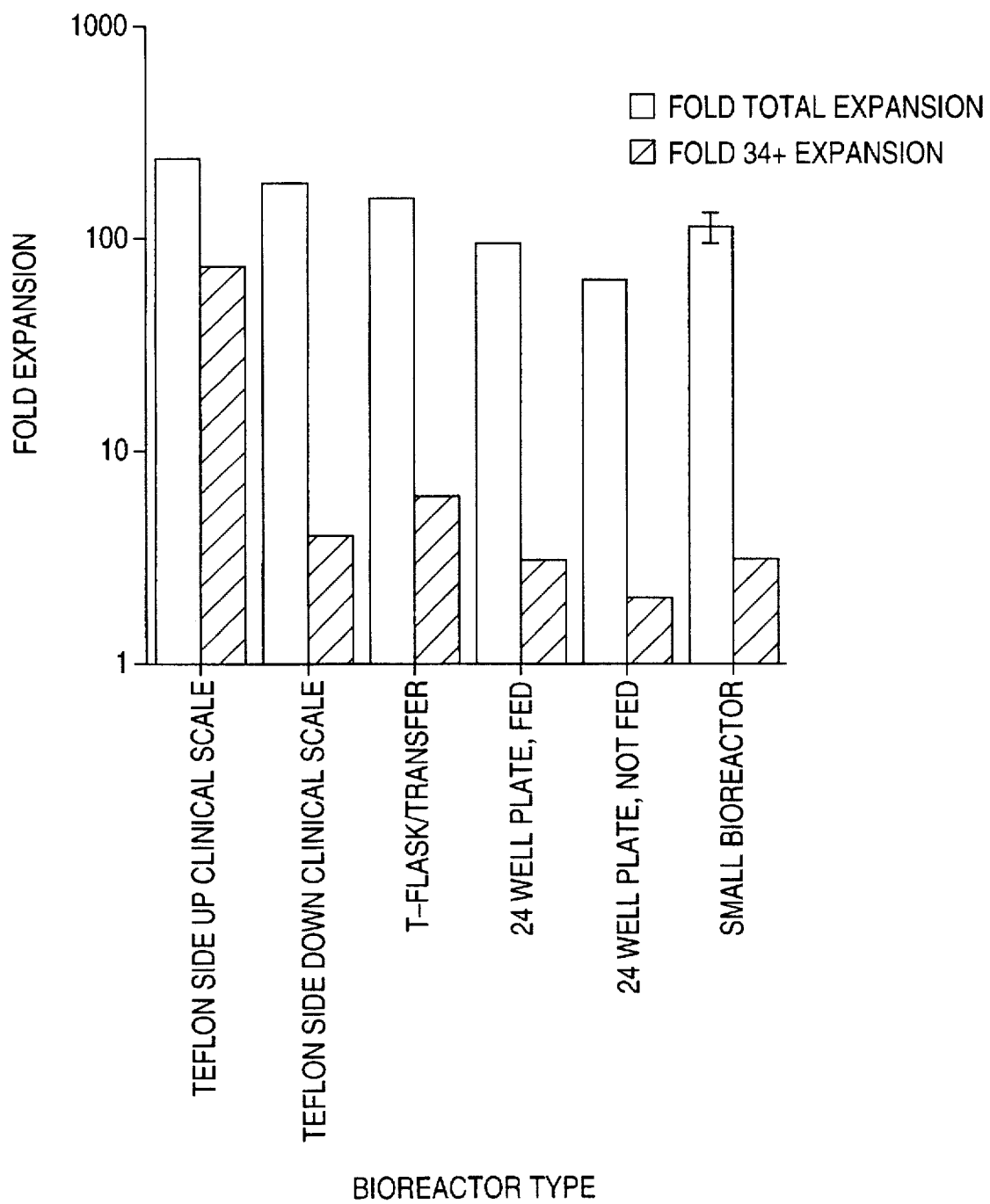
FIG. 5 shows the comparison of a clinical scale bioreactor with open culture systems for expansion of mobilized peripheral blood stem cells.
Figure 6:
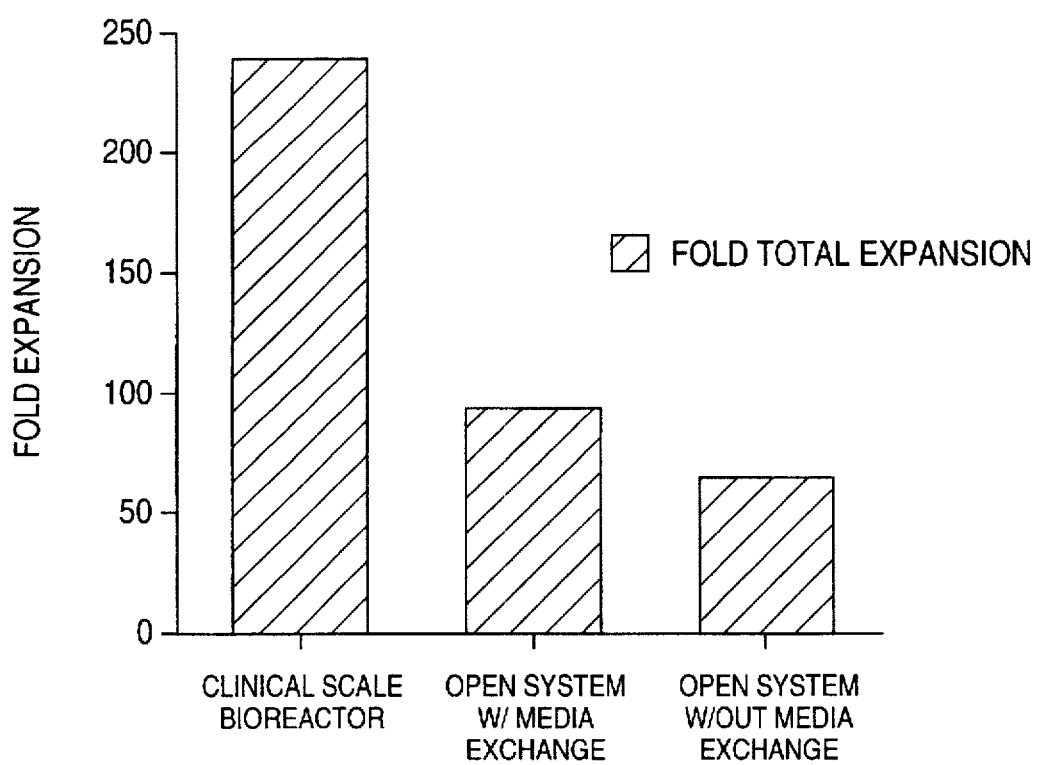
FIG. 6 is a total comparison between a clinical scale bioreactor and open (static) systems for expansion of mobilized peripheral blood stem cells. Each point represents the average of 3 points with the exception of the bioreactor which represents an average of 2 points.
Figure 7:
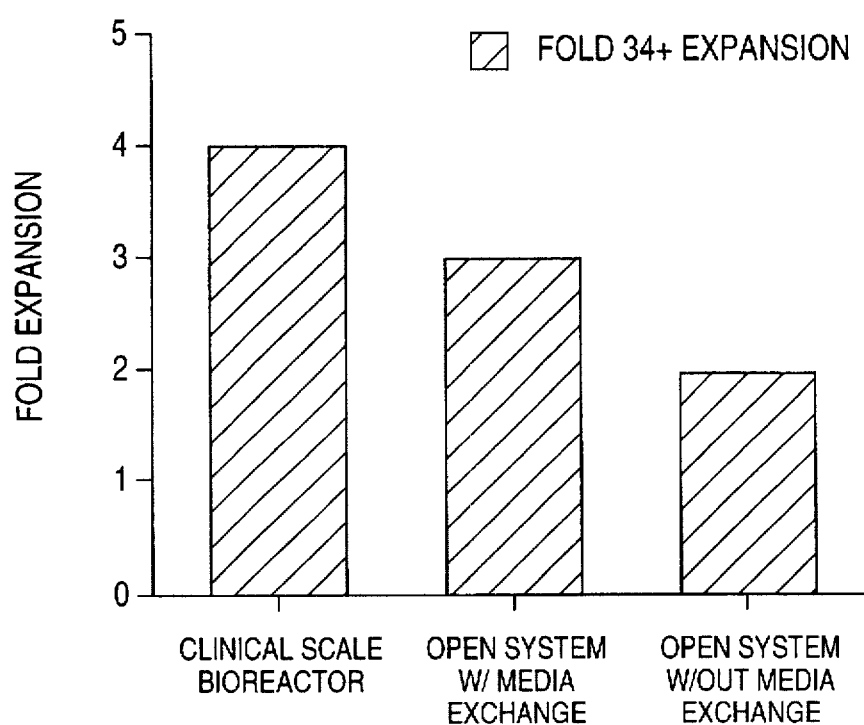
FIG. 7 shows $CD34^+$ phenotype expansion between a clinical scale bioreactor and open (static) systems for expansion of mobilized peripheral blood stem cells. Each point represents the average of 3 points with the exception of the bioreactor which represents an average of 2 points.

The results show that the bioreactor performed better than either 24-well plates or the T-flasks used as controls (See FIGS. 5, 6, and 7) in terms of total cell expansion as well as expansion of CD34$^+$ cells.

Headspace Bioreactor Modification. There is evidence to suggest that oxygen radicals, when coming in contact with cells, cause the cells to differentiate as opposed to expanding clonally. The sandwich bioreactor of this invention has been designed to help alleviate this problem. With the cells resting on the gas-impermeable polycarbonate, the oxygen radicals must permeate the top membrane and diffuse through the liquid layer before reaching the cells. There is thus a strong probability that the oxygen radicals will come in contact with an oxygen radical scavenger in the medium before reaching the cells. However, if the cells rest on the gas permeable membrane, the oxygen radicals can attack the cells directly without being intercepted by a radical scavenger in the medium.

To improve bioreactor performance, a headspace system could be used (See FIG. 10). This system has a gas impermeable bottom membrane with a gas headspace above the surface for gas transfer to the cells. Unlike the sandwich design that uses one gas permeable and one gas impermeable membrane and therefore needs to be "flipped" to keep the culture expanding, the headspace system can reach high cell densities without disturbing its position. The headspace system uses a dip tube to control volume and this tube length can be changed to optimize the medium depth.

Large Scale Expansion of Bone Marrow Stem Cells. Approximately 200,000 Thy-1$^+$ cells are suspended in 10 mL of SSP-10 medium with IL-3 (10 ng/mL) and c-kit ligand (50 ng/mL) and inoculated into a 30 mL flask. This flask is incubated at 37° C., 5% $O_2$, and 5% $CO_2$. Concentrated cytokine is added to the culture on days 4, 7, 10, 13, and 16, and 19. This was done by introducing a 1 mL volume of a 10× concentrated cytokine solution—i.e., 100 µg/mL IL-3 and 500 ng/mL c-kit ligand. On day 10, the volume of the culture medium is increased to 30 mL and the culture is gently shaken to mix. On day 14, perfusion of the medium is initiated at a rate of about 0.25 volume/day. Cells are harvested on day 21.

Large Scale Expansion of Mobilized Blood from a Multiple Myeloma Patient Approximately 200,000 mobilized blood cells are suspended in 10 mL of SSP-10 medium with IL-3 (10 ng/mL), IL-6 (10 ng/mL), G-CSF (10 ng/mL), and c-kit ligand (50 ng/mL) and inoculated into a 30 mL flask. The flask is then incubated at 37° C., 5% $O_2$, and 5% $CO_2$. The cells are allowed to grow and condition the medium for at least 7 days. On day 7, medium is added quickly to the culture to increase the volume to 30 mL. The culture is then gently shaken to mix. On day 10, perfusion of the medium is initiated at a rate of about 0.25/day and increased on day 12 to 0.40/day. Cells are harvested on day 14.

Throughout this application, various publications, patents and published patent applications are referenced within this disclosure to more fully describe the state of the art to which this invention pertains. The disclosures of these publications, patents and published patent applications are incorporated by reference herein.

Although the invention has been described with reference to the disclosed embodiments, those skilled in the art will readily appreciate that the specific experiments are only illustrative of the invention. It should be understood that various modifications can be made without departing from the spirit of the invention. Accordingly, the invention is limited only by the following claims.

What is claimed is:

1. A method for expanding hematopoietic stem cells in a population of cells substantially enriched in hematopoietic stems cells and substantially free of stromal cells, the method comprising the steps of:
   a) inoculating the population of cells in an expansion container in a volume of a suitable medium such that the cell density is at least about 5,000 cells/mL and at an initial oxygen concentration of less than 8%;
   b) adding an effective amount of at least one cytokine to cause stem cell expansion;
   c) culturing the population of cells under suitable conditions for at least 6 days and such that the cells condition the medium;
   d) increasing the oxygen concentration to about 20%;
   e) exchanging the medium at a rate of about 1/10 to 1/2 volume exchanged per day and which allows expansion of the population of hematopoietic stem cells; and
   f) culturing the cells under conditions such that the hematopoietic stem cells are expanded.

2. The method of claim 1, wherein inoculating population of cells is derived from bone marrow and is from about 7,000 cells/mL to about 20,000 cells/mL.

3. The method of claim 1, wherein the inoculation population of cells is derived from mobilized peripheral blood and is from about 20,000 cells/mL to about 50,000 cells/mL.

4. The method of claim 1, wherein the inoculation population of cells is CD34$^+$LIN$^-$.

5. The method of claim 4, wherein the inoculation population of cells is CD34$^+$Thy-1+LIN$^-$.

6. The method of claim 1, wherein the medium is serum free.

7. The method of claim 6, wherein the medium is comprised of IMDM, effective amounts of at least one of a peptone, a protease inhibitor and a pituitary extract and effective amounts of at least one of human serum albumin or, plasma protein fraction, heparin, a reducing agent, insulin, transferrin and ethanolamine.

8. The method of claim 1, wherein the suitable expansion medium comprises IMDM and 1–15% fetal bovine serum.

9. The method of claim 1, wherein the cytokine is selected from the group consisting of c-kit, IL-6, GM-CSF, IL-1α, IL-11, MIP-1α, G-CSF, IL-3, GM-CSF, cmpl ligand and LIF.

10. The method of claim 1, wherein the suitable conditions of step c) comprise an oxygen concentration of about 2–8%.

11. The method of claim 1, wherein the initial oxygen concentration of step (a) is about 5%.

12. The method of claim 1, wherein step c) is under conditions suitable to allow release of autocrine factors without release of sufficient waste products to substantially inhibit stem cell expansion.

13. The method of claim 1, wherein step c) is from about 7 to about 10 days.

14. The method of claim 1, wherein the medium is perfused through the expansion container in a manner sufficient to maintain uniform flow and at a rate which removes waste products and maintains sufficient concentration of autocrine factors to allow stem cell expansion.

15. The method of claim 1, wherein step f) includes growth of the cells over an increased surface area of the expansion container.

16. The method of claim 1, wherein the expansion container of step a) is a 24 well plate or a 12.5 $cm^2$ tissue culture flask.

17. The method of claim 1, wherein the expansion container is a bioreactor and the cells of step a) are inoculated into the bioreactor.

18. The method according to claim 1, wherein the expansion container is a bioreactor comprising:

a) a rigid housing defining a chamber having an upstream end portion and a downstream end portion; and b) multiple ports formed through said housing, and being in the vicinity of said upstream and downstream end portions in fluid communication with said chamber, the number of ports in the vicinity of one of said upstream or downstream portions being greater the number of ports in the vicinity of the other one of said portions, wherein fluid flow is substantially uniform through the ports between the upstream and downstream end portions.

19. The method of claim 18, wherein said bioreactor includes an inner bottom surface facing said chamber, said bottom surface having a depression formed therein to create about 5 to 10 mL container volume wherein the cells are inoculated into the depression in order to increase the local density of the cells.

* * * * *